(12) United States Patent
Greenfield et al.

(10) Patent No.: US 10,729,749 B2
(45) Date of Patent: Aug. 4, 2020

(54) NEURODEGENERATIVE DISORDERS

(71) Applicant: NEURO-BIO LTD, Abingdon, Oxfordshire (GB)

(72) Inventors: Susan Adele Greenfield, Abingdon (GB); Gwenael Pottiez, Abingdon (GB); Sara Esther Garcia-Rates, Abingdon (GB)

(73) Assignee: NEURO-BIO LTD., Abingdon, Oxfordshire (GB)

( * ) Notice: Subject to any disclaimer, the term of this patent is extended or adjusted under 35 U.S.C. 154(b) by 21 days.

(21) Appl. No.: 15/529,468

(22) PCT Filed: Nov. 26, 2015

(86) PCT No.: PCT/GB2015/053601
§ 371 (c)(1),
(2) Date: May 24, 2017

(87) PCT Pub. No.: WO2016/083809
PCT Pub. Date: Jun. 2, 2016

(65) Prior Publication Data
US 2017/0266265 A1 Sep. 21, 2017

(30) Foreign Application Priority Data
Nov. 26, 2014 (GB) ..................................... 1420986

(51) Int. Cl.
| | | |
|---|---|---|
| *A61K 38/08* | (2019.01) | |
| *A61K 38/46* | (2006.01) | |
| *C12N 9/18* | (2006.01) | |
| *C07K 7/06* | (2006.01) | |
| *A61K 45/06* | (2006.01) | |

(52) U.S. Cl.
CPC ............ *A61K 38/465* (2013.01); *A61K 38/08* (2013.01); *A61K 45/06* (2013.01); *C07K 7/06* (2013.01); *C12N 9/18* (2013.01); *C12Y 301/01007* (2013.01)

(58) Field of Classification Search
CPC ........ A61K 38/465; A61K 38/08; C07K 7/06; C12Y 301/01007
See application file for complete search history.

(56) References Cited

U.S. PATENT DOCUMENTS

2002/0054870 A1    5/2002    Greenfield et al.

FOREIGN PATENT DOCUMENTS

| GB | 2516045 | 1/2015 |
| WO | WO 02/42778 A2 | 5/2002 |
| WO | WO 2008/135790 A1 | 11/2008 |

OTHER PUBLICATIONS

Jackowski, British J. of Neurosurgery 9 (1995): 303-317.*
International Search report and written opinion dated Mar. 24, 2016 in PCT/GB2015/053601 filed Nov. 26, 2015, 15 pages.
International Preliminary Report on Patentability dated Feb. 16, 2017 in PCT/GB2015/053601 filed Nov. 26, 2015, 15 pages.
Jean L. et al., "Heterologous Amyloid Seeding: Revisiting the Role of Acetylcholinesterase in Alzheimer's Disease", *Plos One, Public Library of Science*, US, vol. 2, No. 7, Jul. 25, 2007, pp. E652-E654, XP002497354.
Greenfield Susan et al., "Discovering and targeting the basic mechanism of neurodegeneration: The role of peptides from the C-terminus of acetylcholinesterase Non-hydrolytic effects of ache: The actions of peptides derived from the C-terminal and their relevance to neurodegeneration", *Chemico-Biological Interactions, Elsevier Science Irland*, vol. 203, No. 3, Apr. 3, 2013, pp. 543-546, XP028564053.
Garcia-Rates et al., "Additive Toxicity of [beta]-Amyloid by a Novel Bioactive Peptide In Vitro: Possible Implications for Alzheimer's Disease", *Plos One*, vol. 8, No. 2, Feb. 4, 2013, p. e54864, XP55254231.

* cited by examiner

*Primary Examiner* — Robert C Hayes
(74) *Attorney, Agent, or Firm* — Squire Patton Boggs (US) LLP

(57) ABSTRACT

The invention relates to novel peptides, compositions, therapies and methods for treating neurodegenerative disorders, for example Alzheimer's disease.

10 Claims, 27 Drawing Sheets

Specification includes a Sequence Listing.

⌒ A E F H R W S S Y M V H W K ⌒
↪ Cyclisation (cyclic peptide: A E F H R W S S Y M V H W K)

Figure 4a

| Peptide Name | Sequence | SEQ ID No: | H | W | K | A | E | F | H | R | W | S | Y | M | V | H | W | K | A | E | F | H | R | W | S | Y | M | V | H | W | K |
|---|---|---|---|---|---|---|---|---|---|---|---|---|---|---|---|---|---|---|---|---|---|---|---|---|---|---|---|---|---|---|---|
| | | | | | | | | | | | 4 amino acid peptides | | | | | | | | | | | | | | | | | | | | |
| NBP-401 | HWKA | 2 | H | W | K | A | | | | | | | | | | | | | | | | | | | | | | | | | | |
| NBP-402 | WKAE | 3 | | W | K | A | E | | | | | | | | | | | | | | | | | | | | | | | | | |
| NBP-403 | KAEF | 4 | | | K | A | E | F | | | | | | | | | | | | | | | | | | | | | | | | |
| NBP-404 | AEFH | 5 | | | | A | E | F | H | | | | | | | | | | | | | | | | | | | | | | | |
| NBP-405 | EFHR | 6 | | | | | E | F | H | R | | | | | | | | | | | | | | | | | | | | | | |
| NBP-406 | FHRW | 7 | | | | | | F | H | R | W | | | | | | | | | | | | | | | | | | | | | |
| NBP-407 | HRWS | 8 | | | | | | | H | R | W | S | | | | | | | | | | | | | | | | | | | | |
| NBP-408 | RWSS | 9 | | | | | | | | R | W | S | S | | | | | | | | | | | | | | | | | | | |
| NBP-409 | WSSY | 10 | | | | | | | | | W | S | S | Y | | | | | | | | | | | | | | | | | | |
| NBP-410 | SSYM | 11 | | | | | | | | | | S | S | Y | M | | | | | | | | | | | | | | | | | |
| NBP-411 | SYMV | 12 | | | | | | | | | | | S | Y | M | V | | | | | | | | | | | | | | | | |
| NBP-412 | YMVH | 13 | | | | | | | | | | | | Y | M | V | H | | | | | | | | | | | | | | | |
| NBP-413 | MVHW | 14 | | | | | | | | | | | | | M | V | H | W | | | | | | | | | | | | | | |
| NBP-414 | VHWK | 15 | | | | | | | | | | | | | | V | H | W | K | | | | | | | | | | | | | |

Figure 4b

| Peptide Name | Sequence | SEQ ID No: | H | W | K | A | E | F | H | R | W | S | S | Y | M | V | H | W | K | A |
|---|---|---|---|---|---|---|---|---|---|---|---|---|---|---|---|---|---|---|---|---|
| NBP-501 | HWKAE | 16 | H | W | K | A | E | | | | | | | | | | | | | |
| NBP-502 | WKAEF | 17 | | W | K | A | E | F | | | | | | | | | | | | |
| NBP-503 | KAEFH | 18 | | | K | A | E | F | H | | | | | | | | | | | |
| NBP-504 | AEFHR | 19 | | | | A | E | F | H | R | | | | | | | | | | |
| NBP-505 | EFHRW | 20 | | | | | E | F | H | R | W | | | | | | | | | |
| NBP-506 | FHRWS | 21 | | | | | | F | H | R | W | S | | | | | | | | |
| NBP-507 | HRWSS | 22 | | | | | | | H | R | W | S | S | | | | | | | |
| NBP-508 | RWSSY | 23 | | | | | | | | R | W | S | S | Y | | | | | | |
| NBP-509 | WSSYM | 24 | | | | | | | | | W | S | S | Y | M | | | | | |
| NBP-510 | SSYMV | 25 | | | | | | | | | | S | S | Y | M | V | | | | |
| NBP-511 | SYMVH | 26 | | | | | | | | | | | S | Y | M | V | H | | | |
| NBP-512 | YMVHW | 27 | | | | | | | | | | | | Y | M | V | H | W | | |
| NBP-513 | MVHWK | 28 | | | | | | | | | | | | | M | V | H | W | K | |
| NBP-514 | VHWKA | 29 | | | | | | | | | | | | | | V | H | W | K | A |

5 amino acid peptides

Figure 4c

| Peptide Name | Sequence | SEQ ID No: | H | W | K | A | E | F | H | R | W | S | S | Y | M | V | H | W | K | A | E |
|---|---|---|---|---|---|---|---|---|---|---|---|---|---|---|---|---|---|---|---|---|---|
| NBP-601 | HWKAEF | 30 | H | W | K | A | E | F | | | | | | | | | | | | | |
| NBP-602 | WKAEFH | 31 | | W | K | A | E | F | H | | | | | | | | | | | | |
| NBP-603 | KAEFHR | 32 | | | K | A | E | F | H | R | | | | | | | | | | | |
| NBP-604 | AEFHRW | 33 | | | | A | E | F | H | R | W | | | | | | | | | | |
| NBP-605 | EFHRWS | 34 | | | | | E | F | H | R | W | S | | | | | | | | | |
| NBP-606 | FHRWSS | 35 | | | | | | F | H | R | W | S | S | | | | | | | | |
| NBP-607 | HRWSSY | 36 | | | | | | | H | R | W | S | S | Y | | | | | | | |
| NBP-608 | RWSSYM | 37 | | | | | | | | R | W | S | S | Y | M | | | | | | |
| NBP-609 | WSSYMV | 38 | | | | | | | | | W | S | S | Y | M | V | | | | | |
| NBP-610 | SSYMVH | 39 | | | | | | | | | | S | S | Y | M | V | H | | | | |
| NBP-611 | SYMVHW | 40 | | | | | | | | | | | S | Y | M | V | H | W | | | |
| NBP-612 | YMVHWK | 41 | | | | | | | | | | | | Y | M | V | H | W | K | | |
| NBP-613 | MVHWKA | 42 | | | | | | | | | | | | | M | V | H | W | K | A | |
| NBP-614 | VHWKAE | 43 | | | | | | | | | | | | | | V | H | W | K | A | E |

6 amino acid peptides

Figure 4d

| Peptide Name | Sequence | SEQ ID No: | H | W | K | A | E | F | H | R | W | S | Y | M | V | H | W | K | A | E | F | H | R | W | S | Y | M | V | H | W | K |
|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | 7 amino acid peptides | | | | | | | | | |
| NBP-701 | HWKAEFH | 44 | H | W | K | A | E | F | H | | | | | | | | | | | | | | | | | | | | | | |
| NBP-702 | WKAEFHR | 45 | | W | K | A | E | F | H | R | | | | | | | | | | | | | | | | | | | | | |
| NBP-703 | KAEFHRW | 46 | | | K | A | E | F | H | R | W | | | | | | | | | | | | | | | | | | | | |
| NBP-704 | AEFHRWS | 47 | | | | A | E | F | H | R | W | S | | | | | | | | | | | | | | | | | | | |
| NBP-705 | EFHRWSS | 48 | | | | | E | F | H | R | W | S | S | | | | | | | | | | | | | | | | | | |
| NBP-706 | FHRWSSY | 49 | | | | | | F | H | R | W | S | S | Y | | | | | | | | | | | | | | | | | |
| NBP-707 | HRWSSYM | 50 | | | | | | | H | R | W | S | S | Y | M | | | | | | | | | | | | | | | | |
| NBP-708 | RWSSYMV | 51 | | | | | | | | R | W | S | S | Y | M | V | | | | | | | | | | | | | | | |
| NBP-709 | WSSYMVH | 52 | | | | | | | | | W | S | S | Y | M | V | H | | | | | | | | | | | | | | |
| NBP-710 | SSYMVHW | 53 | | | | | | | | | | S | S | Y | M | V | H | W | | | | | | | | | | | | | |
| NBP-711 | SYMVHWK | 54 | | | | | | | | | | | S | Y | M | V | H | W | K | | | | | | | | | | | | |
| NBP-712 | YMVHWKA | 55 | | | | | | | | | | | | Y | M | V | H | W | K | A | | | | | | | | | | | |
| NBP-713 | MVHWKAE | 56 | | | | | | | | | | | | | M | V | H | W | K | A | E | | | | | | | | | | |
| NBP-714 | VHWKAEF | 57 | | | | | | | | | | | | | | V | H | W | K | A | E | F | | | | | | | | | |

Figure 4e

| Peptide Name | SEQ ID No: | H | W | K | A | E | F | H | R | W | S | S | Y | M | V | H | W | K |
|---|---|---|---|---|---|---|---|---|---|---|---|---|---|---|---|---|---|---|
| NBP-801 | 58 | H | W | K | A | E | F | H | R | | | | | | | | | |
| NBP-802 | 59 | | W | K | A | E | F | H | R | W | | | | | | | | |
| NBP-803 | 60 | | | K | A | E | F | H | R | W | S | | | | | | | |
| NBP-804 | 61 | | | | A | E | F | H | R | W | S | S | | | | | | |
| NBP-805 | 62 | | | | | E | F | H | R | W | S | S | Y | | | | | |
| NBP-806 | 63 | | | | | | F | H | R | W | S | S | Y | M | | | | |
| NBP-807 | 64 | | | | | | | H | R | W | S | S | Y | M | V | | | |
| NBP-808 | 65 | | | | | | | | R | W | S | S | Y | M | V | H | | |
| NBP-809 | 66 | | | | | | | | | W | S | S | Y | M | V | H | W | |
| NBP-810 | 67 | | | | | | | | | | S | S | Y | M | V | H | W | K |
| NBP-811 | 68 | | | | | | | | | | | S | Y | M | V | H | W | K | A |
| NBP-812 | 69 | | | | | | | | | | | | Y | M | V | H | W | K | A | E |
| NBP-813 | 70 | | | | | | | | | | | | | M | V | H | W | K | A | E | F |
| NBP-814 | 71 | | | | | | | | | | | | | | V | H | W | K | A | E | F | H |

(8 amino acid peptides)

Figure 4f

| Peptide Name | Sequence | SEQ ID No: | H | W | K | A | E | F | H | R | W | S | Y | M | V | H | W | K | A | E | F | H | R |
|---|---|---|---|---|---|---|---|---|---|---|---|---|---|---|---|---|---|---|---|---|---|---|---|
| | | | | | | | | | | | | | 9 amino acid peptides | | | | | | | | | | |
| NBP-901 | HWKAEFHRW | 72 | H | W | K | A | E | F | H | R | W | | | | | | | | | | | | |
| NBP-902 | WKAEFHRWS | 73 | | W | K | A | E | F | H | R | W | S | | | | | | | | | | | |
| NBP-903 | KAEFHRWSS | 74 | | | K | A | E | F | H | R | W | S | S | | | | | | | | | | |
| NBP-904 | AEFHRWSSY | 75 | | | | A | E | F | H | R | W | S | S | Y | | | | | | | | | |
| NBP-905 | EFHRWSSYM | 76 | | | | | E | F | H | R | W | S | S | Y | M | | | | | | | | |
| NBP-906 | FHRWSSYMV | 77 | | | | | | F | H | R | W | S | S | Y | M | V | | | | | | | |
| NBP-907 | HRWSSYMVH | 78 | | | | | | | H | R | W | S | S | Y | M | V | H | | | | | | |
| NBP-908 | RWSSYMVHW | 79 | | | | | | | | R | W | S | S | Y | M | V | H | W | | | | | |
| NBP-909 | WSSYMVHWK | 80 | | | | | | | | | W | S | S | Y | M | V | H | W | K | | | | |
| NBP-910 | SSYMVHWKA | 81 | | | | | | | | | | S | S | Y | M | V | H | W | K | A | | | |
| NBP-911 | SYMVHWKAE | 82 | | | | | | | | | | | S | Y | M | V | H | W | K | A | E | | |
| NBP-912 | YMVHWKAEF | 83 | | | | | | | | | | | | Y | M | V | H | W | K | A | E | F | |
| NBP-913 | MVHWKAEFH | 84 | | | | | | | | | | | | | M | V | H | W | K | A | E | F | H |
| NBP-914 | VHWKAEFHR | 85 | | | | | | | | | | | | | | V | H | W | K | A | E | F | H | R |

Figure 4g

| Peptide Name | Sequence | SEQ ID No: | H | W | K | A | E | F | H | R | W | S | S | Y | M | V | H | W | K | A | E | F | H | R | W |
|---|---|---|---|---|---|---|---|---|---|---|---|---|---|---|---|---|---|---|---|---|---|---|---|---|---|
| | | | | | | | | | | | 10 amino acid peptides | | | | | | | | | | | | | | |
| NBP-1001 | HWKAEFHRWS | 86 | H | W | K | A | E | F | H | R | W | S | | | | | | | | | | | | | |
| NBP-1002 | WKAEFHRWSS | 87 | | W | K | A | E | F | H | R | W | S | S | | | | | | | | | | | | |
| NBP-1003 | KAEFHRWSSY | 88 | | | K | A | E | F | H | R | W | S | S | Y | | | | | | | | | | | |
| NBP-1004 | AEFHRWSSYM | 89 | | | | A | E | F | H | R | W | S | S | Y | M | | | | | | | | | | |
| NBP-1005 | EFHRWSSYMV | 90 | | | | | E | F | H | R | W | S | S | Y | M | V | | | | | | | | | |
| NBP-1006 | FHRWSSYMVH | 91 | | | | | | F | H | R | W | S | S | Y | M | V | H | | | | | | | | |
| NBP-1007 | HRWSSYMVHW | 92 | | | | | | | H | R | W | S | S | Y | M | V | H | W | | | | | | | |
| NBP-1008 | RWSSYMVHWK | 93 | | | | | | | | R | W | S | S | Y | M | V | H | W | K | | | | | | |
| NBP-1009 | WSSYMVHWKA | 94 | | | | | | | | | W | S | S | Y | M | V | H | W | K | A | | | | | |
| NBP-1010 | SSYMVHWKAE | 95 | | | | | | | | | | S | S | Y | M | V | H | W | K | A | E | | | | |
| NBP-1011 | SYMVHWKAEF | 96 | | | | | | | | | | | S | Y | M | V | H | W | K | A | E | F | | | |
| NBP-1012 | YMVHWKAEFH | 97 | | | | | | | | | | | | Y | M | V | H | W | K | A | E | F | H | | |
| NBP-1013 | MVHWKAEFHR | 98 | | | | | | | | | | | | | M | V | H | W | K | A | E | F | H | R | |
| NBP-1014 | VHWKAEFHRW | 99 | | | | | | | | | | | | | | V | H | W | K | A | E | F | H | R | W |

Figure 4h

| Peptide Name | Sequence | SEQ ID No: | H | W | K | A | E | F | H | R | W | S | S | Y | M | V | H | W | K | A | E | F | H | R | W | S |
|---|---|---|---|---|---|---|---|---|---|---|---|---|---|---|---|---|---|---|---|---|---|---|---|---|---|---|
| NBP-1101 | HWKAEFHRWSS | 100 | H | W | K | A | E | F | H | R | W | S | S | | | | | | | | | | | | | |
| NBP-1102 | WKAEFHRWSSY | 101 | | W | K | A | E | F | H | R | W | S | S | Y | | | | | | | | | | | | |
| NBP-1103 | KAEFHRWSSYM | 102 | | | K | A | E | F | H | R | W | S | S | Y | M | | | | | | | | | | | |
| NBP-1104 | AEFHRWSSYMV | 103 | | | | A | E | F | H | R | W | S | S | Y | M | V | | | | | | | | | | |
| NBP-1105 | EFHRWSSYMVH | 104 | | | | | E | F | H | R | W | S | S | Y | M | V | H | | | | | | | | | |
| NBP-1106 | FHRWSSYMVHW | 105 | | | | | | F | H | R | W | S | S | Y | M | V | H | W | | | | | | | | |
| NBP-1107 | HRWSSYMVHWK | 106 | | | | | | | H | R | W | S | S | Y | M | V | H | W | K | | | | | | | |
| NBP-1108 | RWSSYMVHWKA | 107 | | | | | | | | R | W | S | S | Y | M | V | H | W | K | A | | | | | | |
| NBP-1109 | WSSYMVHWKAE | 108 | | | | | | | | | W | S | S | Y | M | V | H | W | K | A | E | | | | | |
| NBP-1110 | SSYMVHWKAEF | 109 | | | | | | | | | | S | S | Y | M | V | H | W | K | A | E | F | | | | |
| NBP-1111 | SYMVHWKAEFH | 110 | | | | | | | | | | | S | Y | M | V | H | W | K | A | E | F | H | | | |
| NBP-1112 | YMVHWKAEFHR | 111 | | | | | | | | | | | | Y | M | V | H | W | K | A | E | F | H | R | | |
| NBP-1113 | MVHWKAEFHRW | 112 | | | | | | | | | | | | | M | V | H | W | K | A | E | F | H | R | W | |
| NBP-1114 | VHWKAEFHRWS | 113 | | | | | | | | | | | | | | V | H | W | K | A | E | F | H | R | W | S |

11 amino acid peptides

Figure 4i

| Peptide Name | Sequence | SEQ ID No: | H | W | K | A | E | F | H | R | W | S | S | Y | M | V | H | W | K | A | E | F | H | R | W | S | S |
|---|---|---|---|---|---|---|---|---|---|---|---|---|---|---|---|---|---|---|---|---|---|---|---|---|---|---|---|
| NBP-1201 | HWKAEFHRWSSY | 114 | H | W | K | A | E | F | H | R | W | S | S | Y | | | | | | | | | | | | | |
| NBP-1202 | WKAEFHRWSSYM | 115 | | W | K | A | E | F | H | R | W | S | S | Y | M | | | | | | | | | | | | |
| NBP-1203 | KAEFHRWSSYMV | 116 | | | K | A | E | F | H | R | W | S | S | Y | M | V | | | | | | | | | | | |
| NBP-1204 | AEFHRWSSYMVH | 117 | | | | A | E | F | H | R | W | S | S | Y | M | V | H | | | | | | | | | | |
| NBP-1205 | EFHRWSSYMVHW | 118 | | | | | E | F | H | R | W | S | S | Y | M | V | H | W | | | | | | | | | |
| NBP-1206 | FHRWSSYMVHWK | 119 | | | | | | F | H | R | W | S | S | Y | M | V | H | W | K | | | | | | | | |
| NBP-1207 | HRWSSYMVHWKA | 120 | | | | | | | H | R | W | S | S | Y | M | V | H | W | K | A | | | | | | | |
| NBP-1208 | RWSSYMVHWKAE | 121 | | | | | | | | R | W | S | S | Y | M | V | H | W | K | A | E | | | | | | |
| NBP-1209 | WSSYMVHWKAEF | 122 | | | | | | | | | W | S | S | Y | M | V | H | W | K | A | E | F | | | | | |
| NBP-1210 | SSYMVHWKAEFH | 123 | | | | | | | | | | S | S | Y | M | V | H | W | K | A | E | F | H | | | | |
| NBP-1211 | SYMVHWKAEFHR | 124 | | | | | | | | | | | S | Y | M | V | H | W | K | A | E | F | H | R | | | |
| NBP-1212 | YMVHWKAEFHRW | 125 | | | | | | | | | | | | Y | M | V | H | W | K | A | E | F | H | R | W | | |
| NBP-1213 | MVHWKAEFHRWS | 126 | | | | | | | | | | | | | M | V | H | W | K | A | E | F | H | R | W | S | |
| NBP-1214 | VHWKAEFHRWSS | 127 | | | | | | | | | | | | | | V | H | W | K | A | E | F | H | R | W | S | S |

12 amino acid peptides

Figure 4j

| Peptide Name | Sequence | SEQ ID No: |
|---|---|---|
| NBP-1301 | HWKAEFHRWSSYM | 128 |
| NBP-1302 | WKAEFHRWSSYMV | 129 |
| NBP-1303 | KAEFHRWSSYMVH | 130 |
| NBP-1304 | AEFHRWSSYMVHW | 131 |
| NBP-1305 | EFHRWSSYMVHWK | 132 |
| NBP-1306 | FHRWSSYMVHWKA | 133 |
| NBP-1307 | HRWSSYMVHWKAE | 134 |
| NBP-1308 | RWSSYMVHWKAEF | 135 |
| NBP-1309 | WSSYMVHWKAEFH | 136 |
| NBP-1310 | SSYMVHWKAEFHR | 137 |
| NBP-1311 | SYMVHWKAEFHRW | 138 |
| NBP-1312 | YMVHWKAEFHRWS | 139 |
| NBP-1313 | MVHWKAEFHRWSS | 140 |
| NBP-1314 | VHWKAEFHRWSSY | 141 |

13 amino acid peptides

Figure 4k

| Peptide Name | Sequence | SEQ ID No: | H | W | K | A | E | F | H | R | W | S | Y | M | V | H | W | K | A | E | F | H | R | W | S | Y | M | V | H | W | K |
|---|---|---|---|---|---|---|---|---|---|---|---|---|---|---|---|---|---|---|---|---|---|---|---|---|---|---|---|---|---|---|---|
| | | | | | | | | | | | | | | | | 14 amino acid peptides | | | | | | | | | | | | | | | |
| NBP-1401 | HWKAEFHRWSSYMV | 142 | H | W | K | A | E | F | H | R | W | S | Y | M | V | | | | | | | | | | | | | | | | |
| NBP-1402 | WKAEFHRWSSYMVH | 143 | | W | K | A | E | F | H | R | W | S | Y | M | V | H | | | | | | | | | | | | | | | |
| NBP-1403 | KAEFHRWSSYMVHW | 144 | | | K | A | E | F | H | R | W | S | Y | M | V | H | W | | | | | | | | | | | | | | |
| NBP-1404 | AEFHRWSSYMVHWK | 145 | | | | A | E | F | H | R | W | S | Y | M | V | H | W | K | | | | | | | | | | | | | |
| NBP-1405 | EFHRWSSYMVHWKA | 146 | | | | | E | F | H | R | W | S | Y | M | V | H | W | K | A | | | | | | | | | | | | |
| NBP-1406 | FHRWSSYMVHWKAE | 147 | | | | | | F | H | R | W | S | Y | M | V | H | W | K | A | E | | | | | | | | | | | |
| NBP-1407 | HRWSSYMVHWKAEF | 148 | | | | | | | H | R | W | S | Y | M | V | H | W | K | A | E | F | | | | | | | | | | |
| NBP-1408 | RWSSYMVHWKAEFH | 149 | | | | | | | | R | W | S | Y | M | V | H | W | K | A | E | F | H | | | | | | | | | |
| NBP-1409 | WSSYMVHWKAEFHR | 150 | | | | | | | | | W | S | Y | M | V | H | W | K | A | E | F | H | R | | | | | | | | |
| NBP-1410 | SSYMVHWKAEFHRW | 151 | | | | | | | | | | S | S | Y | M | V | H | W | K | A | E | F | H | R | W | | | | | | |
| NBP-1411 | SYMVHWKAEFHRWS | 152 | | | | | | | | | | | S | Y | M | V | H | W | K | A | E | F | H | R | W | S | | | | | |
| NBP-1412 | YMVHWKAEFHRWSS | 153 | | | | | | | | | | | | Y | M | V | H | W | K | A | E | F | H | R | W | S | S | | | | |
| NBP-1413 | MVHWKAEFHRWSSY | 154 | | | | | | | | | | | | | M | V | H | W | K | A | E | F | H | R | W | S | S | Y | | | |
| NBP-1414 | VHWKAEFHRWSSYM | 155 | | | | | | | | | | | | | | V | H | W | K | A | E | F | H | R | W | S | S | Y | M | | |

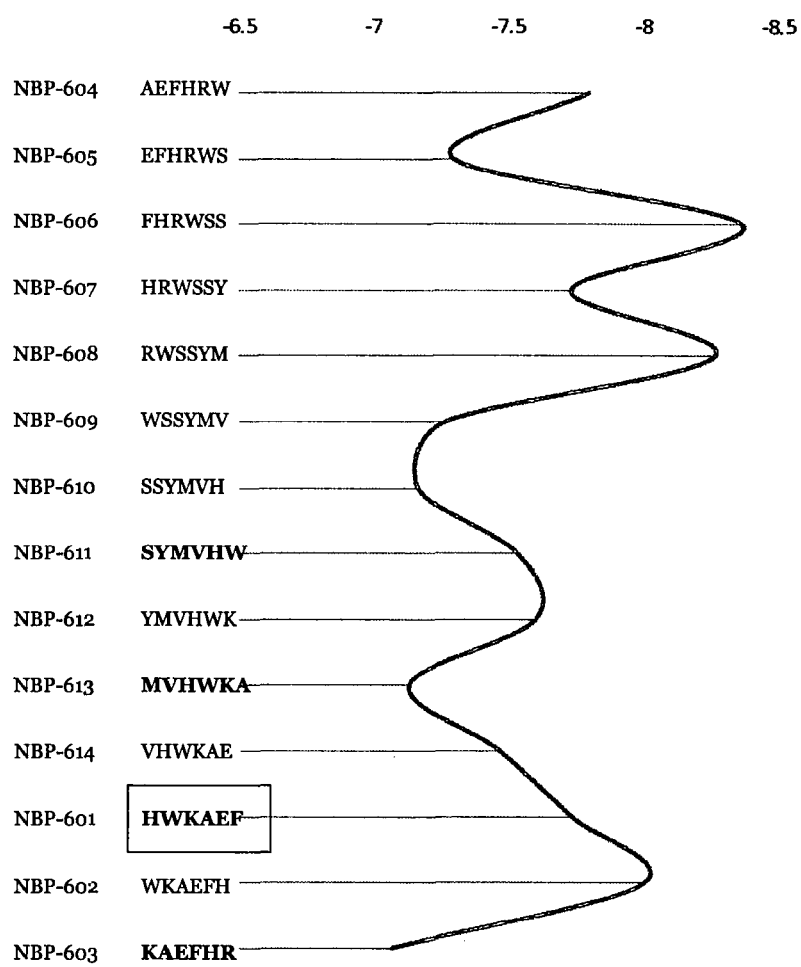

| Concentration | % AChE | % Calcium | % Cell viability |
|---|---|---|---|
| 0.005 | 134.2497 | 130.7359 | 76.25797 |
| 0.007 | 120.8612 | 111.6883 | 67.04465 |
| 0.009 | 113.9162 | 92.78499 | 76.04536 |
| 0.01 | 140.776 | 82.56848 | 71.36782 |
| 0.02 | 115.8328 | 68.90882 | 79.02197 |
| 0.05 | 110.3213 | 65.12369 | 75.1949 |
| 0.06 | 125.9596 | 61.04673 | 62.43799 |
| 0.07 | 99.85138 | 79.43335 | 78.10064 |
| 1 | 115.1942 | 83.9128 | 116.6549 |
| 5 | 79.99317 | 89.55765 | 107.7959 |

| Correlation |
|---|
| 0.210066747 |

Correlation
0.025989854

Correlation
-0.5508289

Calculations to determine the significancy of the Cell viability/AChE correlation value.

r=0.55

N=10 t=-1.863 df=8

Probability=0.049 Significant

Formula used

T=r sqrt n-2/1-r²

NBP 601 (HWKAEF) and NBP 603 (KAEFHR)

This effect corroborates the results in brain slices.

NBP 613 (MVHWKA)

*Protective action*

SEQUENCE LISTING

```
<160> NUMBER OF SEQ ID NOS: 158

<210> SEQ ID NO 1
<211> LENGTH: 14
<212> TYPE: PRT
<213> ORGANISM: Homo sapiens

<400> SEQUENCE: 1

Ala Glu Phe His Arg Trp Ser Ser Tyr Met Val His Trp Lys
1               5                   10

<210> SEQ ID NO 2
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 2

His Trp Lys Ala
1

<210> SEQ ID NO 3
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 3
```

```
Trp Lys Ala Glu
1

<210> SEQ ID NO 4
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 4

Lys Ala Glu Phe
1

<210> SEQ ID NO 5
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 5

Ala Glu Phe His
1

<210> SEQ ID NO 6
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 6

Glu Phe His Arg
1

<210> SEQ ID NO 7
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 7

Phe His Arg Trp
1

<210> SEQ ID NO 8
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 8

His Arg Trp Ser
1

<210> SEQ ID NO 9
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 9
```

-continued

Arg Trp Ser Ser
1

<210> SEQ ID NO 10
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 10

Trp Ser Ser Tyr
1

<210> SEQ ID NO 11
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 11

Ser Ser Tyr Met
1

<210> SEQ ID NO 12
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 12

Ser Tyr Met Val
1

<210> SEQ ID NO 13
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 13

Tyr Met Val His
1

<210> SEQ ID NO 14
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 14

Met Val His Trp
1

<210> SEQ ID NO 15
<211> LENGTH: 4
<212> TYPE: PRT
<213> ORGANISM: Artificial Sequence
<220> FEATURE:
<223> OTHER INFORMATION: A peptide according to the invention

<400> SEQUENCE: 15

Val His Trp Lys

```
<210> SEQ ID NO 16
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 16

His Trp Lys Ala Glu
1               5

<210> SEQ ID NO 17
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 17

Trp Lys Ala Glu Phe
1               5

<210> SEQ ID NO 18
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 18

Lys Ala Glu Phe His
1               5

<210> SEQ ID NO 19
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 19

Ala Glu Phe His Arg
1               5

<210> SEQ ID NO 20
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 20

Glu Phe His Arg Trp
1               5

<210> SEQ ID NO 21
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 21

Phe His Arg Trp Ser
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 22

His Arg Trp Ser Ser
1               5

<210> SEQ ID NO 23
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 23

Arg Trp Ser Ser Tyr
1               5

<210> SEQ ID NO 24
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 24

Trp Ser Ser Tyr Met
1               5

<210> SEQ ID NO 25
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 25

Ser Ser Tyr Met Val
1               5

<210> SEQ ID NO 26
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 26

Ser Tyr Met Val His
1               5

<210> SEQ ID NO 27
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 27

Tyr Met Val His Trp
1               5
```

<210> SEQ ID NO 28
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 28

Met Val His Trp Lys
1               5

<210> SEQ ID NO 29
<211> LENGTH: 5
<212> TYPE: PRT
<213> ORGANISM: Artificial Sequence
<220> FEATURE:
<223> OTHER INFORMATION: A peptide according to the invention

<400> SEQUENCE: 29

Val His Trp Lys Ala
1               5

<210> SEQ ID NO 30
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 30

His Trp Lys Ala Glu Phe
1               5

<210> SEQ ID NO 31
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 31

Trp Lys Ala Glu Phe His
1               5

<210> SEQ ID NO 32
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 32

Lys Ala Glu Phe His Arg
1               5

<210> SEQ ID NO 33
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 33

Ala Glu Phe His Arg Trp
1               5

```
<210> SEQ ID NO 34
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 34

Glu Phe His Arg Trp Ser
1               5

<210> SEQ ID NO 35
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 35

Phe His Arg Trp Ser Ser
1               5

<210> SEQ ID NO 36
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 36

His Arg Trp Ser Ser Tyr
1               5

<210> SEQ ID NO 37
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 37

Arg Trp Ser Ser Tyr Met
1               5

<210> SEQ ID NO 38
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 38

Trp Ser Ser Tyr Met Val
1               5

<210> SEQ ID NO 39
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 39

Ser Ser Tyr Met Val His
1               5

<210> SEQ ID NO 40
```

```
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 40

Ser Tyr Met Val His Trp
1               5

<210> SEQ ID NO 41
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 41

Tyr Met Val His Trp Lys
1               5

<210> SEQ ID NO 42
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 42

Met Val His Trp Lys Ala
1               5

<210> SEQ ID NO 43
<211> LENGTH: 6
<212> TYPE: PRT
<213> ORGANISM: Artificial Sequence
<220> FEATURE:
<223> OTHER INFORMATION: A peptide according to the invention

<400> SEQUENCE: 43

Val His Trp Lys Ala Glu
1               5

<210> SEQ ID NO 44
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 44

His Trp Lys Ala Glu Phe His
1               5

<210> SEQ ID NO 45
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 45

Trp Lys Ala Glu Phe His Arg
1               5

<210> SEQ ID NO 46
<211> LENGTH: 7
```

<212> TYPE: PRT
<213> ORGANISM: Artificial Sequence
<220> FEATURE:
<223> OTHER INFORMATION: A peptide according to the invention

<400> SEQUENCE: 46

Lys Ala Glu Phe His Arg Trp
1               5

<210> SEQ ID NO 47
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 47

Ala Glu Phe His Arg Trp Ser
1               5

<210> SEQ ID NO 48
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 48

Glu Phe His Arg Trp Ser Ser
1               5

<210> SEQ ID NO 49
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 49

Phe His Arg Trp Ser Ser Tyr
1               5

<210> SEQ ID NO 50
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 50

His Arg Trp Ser Ser Tyr Met
1               5

<210> SEQ ID NO 51
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 51

Arg Trp Ser Ser Tyr Met Val
1               5

<210> SEQ ID NO 52
<211> LENGTH: 7
<212> TYPE: PRT

<213> ORGANISM: Artificial Sequence
<220> FEATURE:
<223> OTHER INFORMATION: A peptide according to the invention

<400> SEQUENCE: 52

Trp Ser Ser Tyr Met Val His
1               5

<210> SEQ ID NO 53
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 53

Ser Ser Tyr Met Val His Trp
1               5

<210> SEQ ID NO 54
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 54

Ser Tyr Met Val His Trp Lys
1               5

<210> SEQ ID NO 55
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 55

Tyr Met Val His Trp Lys Ala
1               5

<210> SEQ ID NO 56
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 56

Met Val His Trp Lys Ala Glu
1               5

<210> SEQ ID NO 57
<211> LENGTH: 7
<212> TYPE: PRT
<213> ORGANISM: Artificial Sequence
<220> FEATURE:
<223> OTHER INFORMATION: A peptide according to the invention

<400> SEQUENCE: 57

Val His Trp Lys Ala Glu Phe
1               5

<210> SEQ ID NO 58
<211> LENGTH: 8
<212> TYPE: PRT
<213> ORGANISM: Artificial Sequence

```
<220> FEATURE:
<223> OTHER INFORMATION: A peptide according to the invention

<400> SEQUENCE: 58

His Trp Lys Ala Glu Phe His Arg
1               5

<210> SEQ ID NO 59
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 59

Trp Lys Ala Glu Phe His Arg Trp
1               5

<210> SEQ ID NO 60
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 60

Lys Ala Glu Phe His Arg Trp Ser
1               5

<210> SEQ ID NO 61
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 61

Ala Glu Phe His Arg Trp Ser Ser
1               5

<210> SEQ ID NO 62
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 62

Glu Phe His Arg Trp Ser Ser Tyr
1               5

<210> SEQ ID NO 63
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 63

Phe His Arg Trp Ser Ser Tyr Met
1               5

<210> SEQ ID NO 64
<211> LENGTH: 8
<212> TYPE: PRT
<213> ORGANISM: Artificial Sequence
<220> FEATURE:
```

```
<223> OTHER INFORMATION: A peptide according to the invention

<400> SEQUENCE: 64

His Arg Trp Ser Ser Tyr Met Val
1               5

<210> SEQ ID NO 65
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 65

Arg Trp Ser Ser Tyr Met Val His
1               5

<210> SEQ ID NO 66
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 66

Trp Ser Ser Tyr Met Val His Trp
1               5

<210> SEQ ID NO 67
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 67

Ser Ser Tyr Met Val His Trp Lys
1               5

<210> SEQ ID NO 68
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 68

Ser Tyr Met Val His Trp Lys Ala
1               5

<210> SEQ ID NO 69
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 69

Tyr Met Val His Trp Lys Ala Glu
1               5

<210> SEQ ID NO 70
<211> LENGTH: 8
<212> TYPE: PRT
<213> ORGANISM: Artificial Sequence
<220> FEATURE:
<223> OTHER INFORMATION: A peptide according to the invention
```

```
<400> SEQUENCE: 70

Met Val His Trp Lys Ala Glu Phe
1               5

<210> SEQ ID NO 71
<211> LENGTH: 8
<212> TYPE: PRT
<213> ORGANISM: Artificial Sequence
<220> FEATURE:
<223> OTHER INFORMATION: A peptide according to the invention

<400> SEQUENCE: 71

Val His Trp Lys Ala Glu Phe His
1               5

<210> SEQ ID NO 72
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 72

His Trp Lys Ala Glu Phe His Arg Trp
1               5

<210> SEQ ID NO 73
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 73

Trp Lys Ala Glu Phe His Arg Trp Ser
1               5

<210> SEQ ID NO 74
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 74

Lys Ala Glu Phe His Arg Trp Ser Ser
1               5

<210> SEQ ID NO 75
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 75

Ala Glu Phe His Arg Trp Ser Ser Tyr
1               5

<210> SEQ ID NO 76
<211> LENGTH: 9
<212> TYPE: PRT
<213> ORGANISM: Artificial Sequence
<220> FEATURE:
<223> OTHER INFORMATION: A peptide according to the invention
```

<400> SEQUENCE: 76

Glu Phe His Arg Trp Ser Ser Tyr Met
1               5

<210> SEQ ID NO 77
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 77

Phe His Arg Trp Ser Ser Tyr Met Val
1               5

<210> SEQ ID NO 78
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 78

His Arg Trp Ser Ser Tyr Met Val His
1               5

<210> SEQ ID NO 79
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 79

Arg Trp Ser Ser Tyr Met Val His Trp
1               5

<210> SEQ ID NO 80
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 80

Trp Ser Ser Tyr Met Val His Trp Lys
1               5

<210> SEQ ID NO 81
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 81

Ser Ser Tyr Met Val His Trp Lys Ala
1               5

<210> SEQ ID NO 82
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 82

```
Ser Tyr Met Val His Trp Lys Ala Glu
1               5
```

<210> SEQ ID NO 83
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 83

```
Tyr Met Val His Trp Lys Ala Glu Phe
1               5
```

<210> SEQ ID NO 84
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 84

```
Met Val His Trp Lys Ala Glu Phe His
1               5
```

<210> SEQ ID NO 85
<211> LENGTH: 9
<212> TYPE: PRT
<213> ORGANISM: Artificial Sequence
<220> FEATURE:
<223> OTHER INFORMATION: A peptide according to the invention

<400> SEQUENCE: 85

```
Val His Trp Lys Ala Glu Phe His Arg
1               5
```

<210> SEQ ID NO 86
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 86

```
His Trp Lys Ala Glu Phe His Arg Trp Ser
1               5                   10
```

<210> SEQ ID NO 87
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 87

```
Trp Lys Ala Glu Phe His Arg Trp Ser Ser
1               5                   10
```

<210> SEQ ID NO 88
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 88

Lys Ala Glu Phe His Arg Trp Ser Ser Tyr
1               5                   10

<210> SEQ ID NO 89
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 89

Ala Glu Phe His Arg Trp Ser Ser Tyr Met
1               5                   10

<210> SEQ ID NO 90
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 90

Glu Phe His Arg Trp Ser Ser Tyr Met Val
1               5                   10

<210> SEQ ID NO 91
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 91

Phe His Arg Trp Ser Ser Tyr Met Val His
1               5                   10

<210> SEQ ID NO 92
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 92

His Arg Trp Ser Ser Tyr Met Val His Trp
1               5                   10

<210> SEQ ID NO 93
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 93

His Arg Trp Ser Ser Tyr Met Val His Trp
1               5                   10

<210> SEQ ID NO 94
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 94

Trp Ser Ser Tyr Met Val His Trp Lys Ala

```
<210> SEQ ID NO 95
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 95

Ser Ser Tyr Met Val His Trp Lys Ala Glu
1               5                   10

<210> SEQ ID NO 96
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 96

Ser Tyr Met Val His Trp Lys Ala Glu Phe
1               5                   10

<210> SEQ ID NO 97
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 97

Tyr Met Val His Trp Lys Ala Glu Phe His
1               5                   10

<210> SEQ ID NO 98
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 98

Met Val His Trp Lys Ala Glu Phe His Arg
1               5                   10

<210> SEQ ID NO 99
<211> LENGTH: 10
<212> TYPE: PRT
<213> ORGANISM: Artificial Sequence
<220> FEATURE:
<223> OTHER INFORMATION: A peptide according to the invention

<400> SEQUENCE: 99

Val His Trp Lys Ala Glu Phe His Arg Trp
1               5                   10

<210> SEQ ID NO 100
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 100

His Trp Lys Ala Glu Phe His Arg Trp Ser Ser
1               5                   10
```

<210> SEQ ID NO 101
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 101

Trp Lys Ala Glu Phe His Arg Trp Ser Ser Tyr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 102

Lys Ala Glu Phe His Arg Trp Ser Ser Tyr Met
1               5                   10

<210> SEQ ID NO 103
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 103

Ala Glu Phe His Arg Trp Ser Ser Tyr Met Val
1               5                   10

<210> SEQ ID NO 104
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 104

Glu Phe His Arg Trp Ser Ser Tyr Met Val His
1               5                   10

<210> SEQ ID NO 105
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 105

Phe His Arg Trp Ser Ser Tyr Met Val His Trp
1               5                   10

<210> SEQ ID NO 106
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 106

His Arg Trp Ser Ser Tyr Met Val His Trp Lys
1               5                   10

```
<210> SEQ ID NO 107
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 107

Arg Trp Ser Ser Tyr Met Val His Trp Lys Ala
1               5                   10

<210> SEQ ID NO 108
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 108

Trp Ser Ser Tyr Met Val His Trp Lys Ala Glu
1               5                   10

<210> SEQ ID NO 109
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 109

Ser Ser Tyr Met Val His Trp Lys Ala Glu Phe
1               5                   10

<210> SEQ ID NO 110
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 110

Ser Tyr Met Val His Trp Lys Ala Glu Phe His
1               5                   10

<210> SEQ ID NO 111
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 111

Tyr Met Val His Trp Lys Ala Glu Phe His Arg
1               5                   10

<210> SEQ ID NO 112
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 112

Met Val His Trp Lys Ala Glu Phe His Arg Trp
1               5                   10
```

```
<210> SEQ ID NO 113
<211> LENGTH: 11
<212> TYPE: PRT
<213> ORGANISM: Artificial Sequence
<220> FEATURE:
<223> OTHER INFORMATION: A peptide according to the invention

<400> SEQUENCE: 113

Val His Trp Lys Ala Glu Phe His Arg Trp Ser
1               5                   10

<210> SEQ ID NO 114
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 114

His Trp Lys Ala Glu Phe His Arg Trp Ser Ser Tyr
1               5                   10

<210> SEQ ID NO 115
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 115

Trp Lys Ala Glu Phe His Arg Trp Ser Ser Tyr Met
1               5                   10

<210> SEQ ID NO 116
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 116

Lys Ala Glu Phe His Arg Trp Ser Ser Tyr Met Val
1               5                   10

<210> SEQ ID NO 117
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 117

Ala Glu Phe His Arg Trp Ser Ser Tyr Met Val His
1               5                   10

<210> SEQ ID NO 118
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 118

Glu Phe His Arg Trp Ser Ser Tyr Met Val His Trp
1               5                   10

<210> SEQ ID NO 119
```

```
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 119

Phe His Arg Trp Ser Ser Tyr Met Val His Trp Lys
1               5                   10

<210> SEQ ID NO 120
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 120

His Arg Trp Ser Ser Tyr Met Val His Trp Lys Ala
1               5                   10

<210> SEQ ID NO 121
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 121

Arg Trp Ser Ser Tyr Met Val His Trp Lys Ala Glu
1               5                   10

<210> SEQ ID NO 122
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 122

Trp Ser Ser Tyr Met Val His Trp Lys Ala Glu Phe
1               5                   10

<210> SEQ ID NO 123
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 123

Ser Ser Tyr Met Val His Trp Lys Ala Glu Phe His
1               5                   10

<210> SEQ ID NO 124
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 124

Ser Tyr Met Val His Trp Lys Ala Glu Phe His Arg
1               5                   10

<210> SEQ ID NO 125
<211> LENGTH: 12
```

```
<212> TYPE: PRT
<213> ORGANISM: Artificial Sequence
<220> FEATURE:
<223> OTHER INFORMATION: A peptide according to the invention

<400> SEQUENCE: 125

Tyr Met Val His Trp Lys Ala Glu Phe His Arg Trp
1               5                   10

<210> SEQ ID NO 126
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 126

Met Val His Trp Lys Ala Glu Phe His Arg Trp Ser
1               5                   10

<210> SEQ ID NO 127
<211> LENGTH: 12
<212> TYPE: PRT
<213> ORGANISM: Artificial Sequence
<220> FEATURE:
<223> OTHER INFORMATION: A peptide according to the invention

<400> SEQUENCE: 127

Val His Trp Lys Ala Glu Phe His Arg Trp Ser Ser
1               5                   10

<210> SEQ ID NO 128
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 128

His Trp Lys Ala Glu Phe His Arg Trp Ser Ser Tyr Met
1               5                   10

<210> SEQ ID NO 129
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 129

Trp Lys Ala Glu Phe His Arg Trp Ser Ser Tyr Met Val
1               5                   10

<210> SEQ ID NO 130
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 130

Lys Ala Glu Phe His Arg Trp Ser Ser Tyr Met Val His
1               5                   10

<210> SEQ ID NO 131
<211> LENGTH: 13
<212> TYPE: PRT
```

```
<213> ORGANISM: Artificial Sequence
<220> FEATURE:
<223> OTHER INFORMATION: A peptide according to the invention

<400> SEQUENCE: 131

Ala Glu Phe His Arg Trp Ser Ser Tyr Met Val His Trp
1               5                   10

<210> SEQ ID NO 132
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 132

Glu Phe His Arg Trp Ser Ser Tyr Met Val His Trp Lys
1               5                   10

<210> SEQ ID NO 133
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 133

Phe His Arg Trp Ser Ser Tyr Met Val His Trp Lys Ala
1               5                   10

<210> SEQ ID NO 134
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 134

His Arg Trp Ser Ser Tyr Met Val His Trp Lys Ala Glu
1               5                   10

<210> SEQ ID NO 135
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 135

Arg Trp Ser Ser Tyr Met Val His Trp Lys Ala Glu Phe
1               5                   10

<210> SEQ ID NO 136
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 136

Trp Ser Ser Tyr Met Val His Trp Lys Ala Glu Phe His
1               5                   10

<210> SEQ ID NO 137
<211> LENGTH: 13
<212> TYPE: PRT
<213> ORGANISM: Artificial Sequence
```

```
<220> FEATURE:
<223> OTHER INFORMATION: A peptide according to the invention

<400> SEQUENCE: 137

Ser Ser Tyr Met Val His Trp Lys Ala Glu Phe His Arg
1               5                   10

<210> SEQ ID NO 138
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 138

Ser Tyr Met Val His Trp Lys Ala Glu Phe His Arg Trp
1               5                   10

<210> SEQ ID NO 139
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 139

Tyr Met Val His Trp Lys Ala Glu Phe His Arg Trp Ser
1               5                   10

<210> SEQ ID NO 140
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 140

Met Val His Trp Lys Ala Glu Phe His Arg Trp Ser Ser
1               5                   10

<210> SEQ ID NO 141
<211> LENGTH: 13
<212> TYPE: PRT
<213> ORGANISM: Artificial Sequence
<220> FEATURE:
<223> OTHER INFORMATION: A peptide according to the invention

<400> SEQUENCE: 141

Val His Trp Lys Ala Glu Phe His Arg Trp Ser Ser Tyr
1               5                   10

<210> SEQ ID NO 142
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 142

His Trp Lys Ala Glu Phe His Arg Trp Ser Ser Tyr Met Val
1               5                   10

<210> SEQ ID NO 143
<211> LENGTH: 14
<212> TYPE: PRT
<213> ORGANISM: Artificial Sequence
<220> FEATURE:
```

```
<223> OTHER INFORMATION: A peptide according to the invention

<400> SEQUENCE: 143

Trp Lys Ala Glu Phe His Arg Trp Ser Ser Tyr Met Val His
1               5                   10

<210> SEQ ID NO 144
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 144

Lys Ala Glu Phe His Arg Trp Ser Ser Tyr Met Val His Trp
1               5                   10

<210> SEQ ID NO 145
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 145

Ala Glu Phe His Arg Trp Ser Ser Tyr Met Val His Trp Lys
1               5                   10

<210> SEQ ID NO 146
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 146

Glu Phe His Arg Trp Ser Ser Tyr Met Val His Trp Lys Ala
1               5                   10

<210> SEQ ID NO 147
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 147

Phe His Arg Trp Ser Ser Tyr Met Val His Trp Lys Ala Glu
1               5                   10

<210> SEQ ID NO 148
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 148

His Arg Trp Ser Ser Tyr Met Val His Trp Lys Ala Glu Phe
1               5                   10

<210> SEQ ID NO 149
<211> LENGTH: 14
<212> TYPE: PRT
<213> ORGANISM: Artificial Sequence
<220> FEATURE:
<223> OTHER INFORMATION: A peptide according to the invention
```

```
<400> SEQUENCE: 149

Arg Trp Ser Ser Tyr Met Val His Trp Lys Ala Glu Phe His
1               5                   10

<210> SEQ ID NO 150
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 150

Trp Ser Ser Tyr Met Val His Trp Lys Ala Glu Phe His Arg
1               5                   10

<210> SEQ ID NO 151
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 151

Ser Ser Tyr Met Val His Trp Lys Ala Glu Phe His Arg Trp
1               5                   10

<210> SEQ ID NO 152
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 152

Ser Tyr Met Val His Trp Lys Ala Glu Phe His Arg Trp Ser
1               5                   10

<210> SEQ ID NO 153
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 153

Tyr Met Val His Trp Lys Ala Glu Phe His Arg Trp Ser Ser
1               5                   10

<210> SEQ ID NO 154
<211> LENGTH: 14
<212> TYPE: PRT
<213> ORGANISM: Artificial Sequence
<220> FEATURE:
<223> OTHER INFORMATION: A peptide according to the invention

<400> SEQUENCE: 154

Met Val His Trp Lys Ala Glu Phe His Arg Trp Ser Ser Tyr
1               5                   10

<210> SEQ ID NO 155
<211> LENGTH: 14
<212> TYPE: PRT
<213> ORGANISM: Artificial Sequence
<220> FEATURE:
<223> OTHER INFORMATION: A peptide according to the invention
```

-continued

```
<400> SEQUENCE: 155

Val His Trp Lys Ala Glu Phe His Arg Trp Ser Ser Tyr Met
1               5                   10

<210> SEQ ID NO 156
<211> LENGTH: 30
<212> TYPE: PRT
<213> ORGANISM: Artificial Sequence
<220> FEATURE:
<223> OTHER INFORMATION: Linear, T30 peptide

<400> SEQUENCE: 156

Lys Ala Glu Phe His Arg Trp Ser Ser Tyr Met Val His Trp Lys Asn
1               5                   10                  15

Gln Phe Asp His Tyr Ser Lys Gln Asp Arg Cys Ser Asp Leu
            20                  25                  30

<210> SEQ ID NO 157
<211> LENGTH: 614
<212> TYPE: PRT
<213> ORGANISM: Artificial Sequence
<220> FEATURE:
<223> OTHER INFORMATION: Amino acid sequence of the tail of human
      acetylcholinesterase

<400> SEQUENCE: 157

Met Arg Pro Pro Gln Cys Leu Leu His Thr Pro Ser Leu Ala Ser Pro
1               5                   10                  15

Leu Leu Leu Leu Leu Leu Trp Leu Leu Gly Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255
```

```
Val Leu Gln Ser Gly Ala Pro Asn Gly Pro Trp Ala Thr Val Gly Met
            260                 265                 270

Gly Glu Ala Arg Arg Ala Thr Gln Leu Ala His Leu Val Gly Cys
        275                 280                 285

Pro Pro Gly Gly Thr Gly Gly Asn Asp Thr Glu Leu Val Ala Cys Leu
290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
                325                 330                 335

Asp Phe Leu Ser Asp Thr Pro Glu Ala Leu Ile Asn Ala Gly Asp Phe
            340                 345                 350

His Gly Leu Gln Val Leu Val Gly Val Val Lys Asp Glu Gly Ser Tyr
        355                 360                 365

Phe Leu Val Tyr Gly Ala Pro Gly Phe Ser Lys Asp Asn Glu Ser Leu
370                 375                 380

Ile Ser Arg Ala Glu Phe Leu Ala Gly Val Arg Val Gly Val Pro Gln
385                 390                 395                 400

Val Ser Asp Leu Ala Ala Glu Ala Val Val Leu His Tyr Thr Asp Trp
                405                 410                 415

Leu His Pro Glu Asp Pro Ala Arg Leu Arg Glu Ala Leu Ser Asp Val
            420                 425                 430

Val Gly Asp His Asn Val Val Cys Pro Val Ala Gln Leu Ala Gly Arg
        435                 440                 445

Leu Ala Ala Gln Gly Ala Arg Val Tyr Ala Tyr Val Phe Glu His Arg
450                 455                 460

Ala Ser Thr Leu Ser Trp Pro Leu Trp Met Gly Val Pro His Gly Tyr
465                 470                 475                 480

Glu Ile Glu Phe Ile Phe Gly Ile Pro Leu Asp Pro Ser Arg Asn Tyr
                485                 490                 495

Thr Ala Glu Glu Lys Ile Phe Ala Gln Arg Leu Met Arg Tyr Trp Ala
            500                 505                 510

Asn Phe Ala Arg Thr Gly Asp Pro Asn Glu Pro Arg Asp Pro Lys Ala
        515                 520                 525

Pro Gln Trp Pro Pro Tyr Thr Ala Gly Ala Gln Gln Tyr Val Ser Leu
530                 535                 540

Asp Leu Arg Pro Leu Glu Val Arg Arg Gly Leu Arg Ala Gln Ala Cys
545                 550                 555                 560

Ala Phe Trp Asn Arg Phe Leu Pro Lys Leu Leu Ser Ala Thr Asp Thr
                565                 570                 575

Leu Asp Glu Ala Glu Arg Gln Trp Lys Ala Glu Phe His Arg Trp Ser
            580                 585                 590

Ser Tyr Met Val His Trp Lys Asn Gln Phe Asp His Tyr Ser Lys Gln
        595                 600                 605

Asp Arg Cys Ser Asp Leu
    610

<210> SEQ ID NO 158
<211> LENGTH: 42
<212> TYPE: PRT
<213> ORGANISM: Artificial Sequence
<220> FEATURE:
<223> OTHER INFORMATION: Beta-amyloid protein

<400> SEQUENCE: 158
```

```
Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35              40
```

NEURODEGENERATIVE DISORDERS

This application claims priority to, and the benefit of, International PCT Patent Application No. PCT/GB2015/053601, entitled NEURODEGENERATIVE DISORDERS, filed Nov. 26, 2015, which claims priority from GB Application 1420986.0, filed Nov. 26, 2014, the disclosure of each of which is incorporated herein by reference in their entirety for all purposes.

The invention relates to neurodegenerative disorders, and in particular to novel peptides, compositions, therapies and methods for treating such conditions, for example Alzheimer's disease.

Alzheimer's disease primarily affects men and women over the age of 65 and the likelihood of being diagnosed with the disease increases substantially with age. With the percentage of adults over the age of 65 expected to grow worldwide over the next 40 years, the incidence of Alzheimer's disease is expected to more than double, escalating from 21 million cases in 2010 to 53 million in 2050 (statistics from www.alzheimersresearchuk.org and www.alz.org). This exponential increase in the expected number of patients presenting with Alzheimer's disease not only represents a major area of unmet medical need, but offers a significant market opportunity for therapeutics and diagnostics as there is currently no fully effective method of treating the disease.

There has been no new drug to combat Alzheimer's disease specifically, nor neurodegeneration more generally, in the last 10 years. The reason is that as yet, the basic underlying brain mechanism has not yet been identified that could consequently be targeted pharmaceutically. The main contender for accounting for the process of neurodegeneration is the 'amyloid hypothesis', where neuronal death is attributed to disruption of the cell membrane by toxic deposits of amyloid, characteristic of post-mortem Alzheimer brain, and resulting from abnormal cleavage of amyloid precursor protein. However, this 'amyloid hypothesis' does not explain the co-pathology frequently observed with Alzheimer's and Parkinson's diseases, nor the characteristic selectivity of cells vulnerable to degeneration despite the potential ubiquity of amyloid in all brain cells, nor the absence of amyloid deposits in animal models of dementia, nor indeed the occurrence of amyloid in certain brain regions where cognitive deficits are not apparent. Despite the popularity of amyloid formation as a pharmaceutical target over the last two decades, no treatment based on this theory has as yet proved effective. A more likely possibility is that once the neurodegenerative process is underway, then amyloid will additionally be generated as a secondary, exacerbating effect that is less specific.

One clue for identifying the primary mechanism of neurodegeneration, could be that only various neuronal groups are primarily vulnerable. Moreover, the diverse cell sub-groups prone to Alzheimer's, Parkinson's and Motor Neurone Diseases nonetheless are adjacent to each other and form a continuous 'hub' extending from brainstem to forebrain that all send diffuse projections upwards and outwards to higher cerebral centres. Hence, despite their heterogeneity in transmitters, these neuronal groups have been collectively dubbed 'Global' neurons to distinguish them from the more familiar and localised circuits of cells in most other parts of the brain, such as cerebellum, thalamus, cortex etc. These selectively vulnerable Global neurons were previously identified, albeit using a different terminology ('isodendritic core') as pivotal in neurodegeneration several decades ago.

The sub-groups of Global neurons have a specific feature in common that might explain the puzzling and as yet unanswered question as to why only these cells succumb to progressive death whilst their counterparts elsewhere in the brain, even when damaged by stroke, do not: they retain a robust plasticity into and throughout adulthood, accompanied by a specific sensitivity to substances aiding and sustaining growth—'trophic factors'. In the developing brain, trophic factors work by stimulating calcium influx, which triggers a cascade of events within the cell, eventually resulting in selective differentiation and growth. However, in higher doses or with longer exposures, sustained calcium entry can be toxic to neurons. Most significantly, a further determining factor in whether or not calcium entry triggers trophic or toxic effects, is age: as neurons mature, an erstwhile trophic level of intracellular calcium becomes lethal.

The inventors have previously proposed that the neurodegenerative process is in fact an aberrantly activated process of development. In support of this hypothesis, a hypertrophy of the brainstem 'hub' neurons has actually been reported in Alzheimer brains (Bowser et al., 1997, Brain Pathol. 7:723-30). If large areas of this hub are damaged, then more than one neurodegenerative disease will present, as occurs in the frequently seen but never as yet explained cases of co-pathology with Alzheimer's and Parkinson's diseases. Interestingly, all the neurons within the vulnerable hub of Global neurons, despite transmitter heterogeneity, all contain the familiar enzyme acetylcholinesterase (AChE). AChE is therefore present in neurons where it would be unable to perform its normal function, since such sub-groups of cells as the noradrenergic locus coeruleus, the dopaminergic substantia nigra, or the serotonergic raphe nuclei, in no cases contain the usual substrate, acetylcholine. A further unexpected deviation from its normal, enzymatic role is that the AChE is actually released from Global neurons, presumably as some kind of inter-cellular messenger in its own right. In general, AChE is now widely and well-established as a signalling molecule that has trophic activity in a diverse variety of situations in both neural and non-neural tissue.

The inventors have previously shown that AChE, operating as a trophic agent independent of its enzymatic action, does indeed trigger calcium entry into neurons. It is possible therefore that within Global neurons, AChE has a dual non-classical action that ranges along a trophic-toxic axis, depending on amount, duration of availability and, most significantly, age. If standard neurons are damaged in adulthood, as in a stroke, others will compensate functionally. In contrast, Global neurons will respond by calling on their trophic resources in an attempt to regenerate. But because the subsequent calcium influx will be lethal in the older, mature cells, the resulting damage will trigger further attempts to compensate in a pernicious cycle that characterises neurodegeneration.

Acetylcholinesterase (AChE) is expressed at different stages of development in various forms, all of which have identical enzymatic activity, but which have very different molecular composition. The 'tailed' (T-AChE) is expressed at synapses and the inventors have previously identified two peptides that could be cleaved from the C-terminus, one referred to as "T14", within the other which is known as "T30", and which both have strong sequence homology to the comparable region of β-amyloid. The AChE C-terminal peptide "T14'" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE, where the inert residue within the T30 sequence (i.e. "T15") is without effect.

Acute effects of T14 and T30 are that they:—(i) modulate calcium entry into neurons in brain slices over time scales from milliseconds to hours; (ii) compromise cell viability in PC12 cells and also in neuronal organotypic cultures in vitro; (iii) modulate 'compensatory' calcium-induced AChE release from neurons and PC12 cells; (iv) activate calcium currents in oocytes and neurons in brain slices; (v) synergise with amyloid in toxic effects; and (vi) are involved in amyloid precursor protein production and amyloid beta (Aβ) peptide release. Chronic effects of T14 and T30 are that they:—(i) reduce neuron growth; (ii) induce apoptosis; (iii) increase AChE release; (iv) bind to and modulate α7 nicotinic-receptor; and (v) enhance expression of the α7 receptor on the cell surface over 24 hours, thereby providing a feedforward mechanism for further toxicity.

Since T14 and T30 are more selective than β-amyloid in inducing toxicity and are also synergistic with amyloid exacerbating toxicity, it has been postulated that any agent which blocks the toxic effects of T14 or T30 would also reduce the less selective and subsequent toxic effect of amyloid. The inventor has previously shown that T30 and T14 peptides bind to an allosteric site on the α7 nicotinic-receptor to induce a spectrum of trophic-toxic effects. This receptor is co-expressed with AChE during critical periods of brain development as well as showing a closely parallel distribution in the adult brain, and is one of the most powerful calcium ionophores in the brain. It can also function independent of cholinergic transmission, since choline (derived from diet) can serve as an alternative primary ligand. Moreover, this receptor has already been implicated in Alzheimer's disease as one of the targets for the current therapy galanthamine (Reminyl®), as well as being linked to the actions of amyloid.

However, the efficacy of galanthamine has proved limited, whilst other α7 nicotinic acetylcholine receptor antagonists are still in clinical trials. Not only does galanthamine have non-specific effects on other receptors, as well as inhibiting AChE, but it has a low affinity for the α7 nicotinic-receptor (i.e. only 10 µM) compared to that of T30 and T14, which have much higher affinities for the α7 nicotinic-receptor (i.e. 5 nM). Hence if, in an Alzheimer's brain, the endogenous equivalent of the T30 peptide is already occupying the respective receptor site, galanthamine would need to be given at non-physiological, high doses with inevitable side effects and most importantly, questionable efficacy.

The inventors have previously shown that cyclic polypeptides comprising an amino acid sequence derived from the C-terminus of acetylcholinesterase (AChE) selectively inhibit the non-classical effects of AChE (i.e. the effects of AChE that are independent of its enzymatic activity) and/or its terminal peptide in vitro, and therefore can be used to treat neurodegenerative disorders. For example, the cyclic peptide referred to as "NBP14", which is shown in FIGS. 2 and 3, has been shown to be particularly active, as it acts as an allosteric modulator of the α7 nicotinic-receptor antagonizing the effects of AChE peptides and Amyloid beta. It was shown to protect cells from linear T14, T30 and β-amyloid toxicity, and it blocks compensatory AChE release induced by the toxicity of linear T14 and T30. In addition, they observed that cyclic NBP14 given alone has no significant effects on $Ca^{2+}$ concentrations in rat brain slices, but blocks the effects of β-amyloid.

However, in spite of the activity exhibited by cyclic NBP14, due to its size, there are some concerns of its ability to cross the blood-brain barrier. Therefore, there is an ongoing need to provide improved medicaments for the treatment of neurodegenerative disorders, such as Alzheimer's disease and Parkinson's disease.

As discussed in the Examples, the inventors built on their previous work by turning their attention to small linear peptides (i.e. 4-14 amino acids in length) derived from the C-terminus of acetylcholinesterase (AChE), or cyclic variants thereof. They have produced an array of peptides, and found that it is surprisingly possible to categorize active linear peptides, which are useful for treating neurodegenerative disorders, and separate them from inactive linear peptides, which are not useful. These active and inactive peptides are categorized on the basis of their neuroprotective efficacy against T30 or amyloid, as measured by a reduction in cell loss and concomitant compensatory release of AChE, i.e. a value coefficient which is determined by calculating the percentage of acetylcholinesterase released from PC12 cells cultured in the presence of the linear peptide compared to that of PC12 cells in the absence of the peptide, and dividing this value by the percentage of viability of PC12 cells in the presence of the peptide.

Thus, according to a first aspect of the invention, there is provided a peptide, derivative or analogue thereof comprising or consisting of a sequence of 5 to 8 amino acids which are derived from the C-terminus of acetylcholinesterase (AChE), or a cyclic variant or a truncation thereof, wherein the peptide, derivative or analogue thereof has a value coefficient, x, of 1.0 to 1.1, wherein $$x = \frac{\%\ AChE\ \text{release}}{\%\ PC_{12}\ \text{cell viability}},$$

wherein "% AChE release" is the percentage of acetylcholinesterase released from a PC12 cell preparation cultured in the presence of a toxic peptide selected from T30 (SEQ ID No: 156) or Aβ (SEQ ID No:158), and the peptide, derivative or analogue thereof, compared to that of the PC12 cell preparation cultured in the absence of any peptide, derivative or analogue thereof (i.e. control), and "% PC12 cell viability" is the percentage viability of the PC12 cell preparation cultured in the presence of the toxic peptide selected from T30 (SEQ ID No: 156) or Aβ (SEQ ID No:158), and the peptide, derivative or analogue thereof, compared to that of a PC12 cell preparation cultured in the absence of any peptide, derivative or analogue thereof (i.e. control).

As described in the Examples, the inventors have surprisingly shown that it is possible to separate active from inactive peptides based on their value coefficients (X) which represent their protective efficacy against T30 and Aβ toxicity. The control value (i.e. absence of peptide is 1.0. The value coefficient is a relation of two biological parameters, wherein x=1.0 to 1.1 means no toxicity or protective, and wherein x>1.1 means toxicity. The value for T30 is x=169.45/74.309=2.28, and for Amyloid Beta (Aβ) x=124.19/87.42=1.42.

Tables 1 and 2 show the effects of the linear peptides on AChE activity and PC12 cell viability against T30 and Aβ toxicity. As can be seen, some peptides are protective whereas others do not prevent toxicity. It could not have been predicted that the peptides of the invention would outcompete the endogenous equivalent of T30 peptide already occupying the respective receptor site. Accordingly, the peptide of the first aspect prevents the previously established toxic effects of the linear T30 (and T14) peptides and also β-amyloid (Aβ). Another criterion is that the active peptide are 5-8 amino acids in length, since compounds of greater size are believed to have less likelihood of gaining access to the brain from the periphery, i.e. cross the blood-brain barrier. Accordingly, use of the two criteria (i.e. amino acid length and neuroprotective activity) enables the isolation of neuroprotective linear peptides by structure as well as by function. As such, the inventors are confident of their efficacy in vivo, and believe that the peptides of the invention will have significant utility for the treatment of neurodegenerative disorders in stabilising any further cell loss.

In a second aspect of the invention, there is provided one or more peptide, derivative or analogue thereof according to the first aspect, for use in therapy or diagnosis.

In a third aspect, there is provided one or more peptide, derivative or analogue thereof according to the first aspect, for use in treating, ameliorating or preventing a neurodegenerative disorder.

In a fourth aspect, there is provided a method of treating, ameliorating or preventing a neurodegenerative disorder in a subject, the method comprising, administering to a subject in need of such treatment, a therapeutically effective amount of one or more peptide, derivative or analogue thereof according to the first aspect.

The neurodegenerative disorder which is treated is preferably one each is characterised by the damage or death of 'Global' neurons. For example, the neurodegenerative disorder may be selected from a group consisting of Alzheimer's disease; Parkinson's disease; Huntington's disease; Motor Neurone disease; Spinocerebellar type 1, type 2, and type 3; Amyotrophic Lateral Sclerosis (ALS); schizophrenia; Lewy-body dementia; and Frontotemporal Dementia.

Preferably, the neurodegenerative disorder, which is treated, is Alzheimer's disease, Parkinson's disease, or Motor Neurone disease. Most preferably, the neurodegenerative disorder, which is treated with the peptide, derivative or analogue thereof according to the first aspect, is Alzheimer's disease.

The term "derivative or analogue thereof" can mean a peptide within which amino acid residues are replaced by residues (whether natural amino acids, non-natural amino acids or amino acid mimics) with similar side chains or peptide backbone properties. Additionally, the terminals of such peptides may be protected by N- and C-terminal protecting groups with similar properties to acetyl or amide groups.

Derivatives and analogues of peptides according to the invention may also include those that increase the peptide's half-life in vivo. For example, a derivative or analogue of the peptides of the invention may include peptoid and retropeptoid derivatives of the peptides, peptide-peptoid hybrids and D-amino acid derivatives of the peptides.

Peptoids, or poly-N-substituted glycines, are a class of peptidomimetics whose side chains are appended via the nitrogen atom of the peptide backbone, rather than to the alpha-carbons, as they are in amino acids. Peptoid derivatives of the peptides of the invention may be readily designed from knowledge of the structure of the peptide. Retropeptoids (in which all amino acids are replaced by peptoid residues in reversed order) are also suitable derivatives in accordance with the invention. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

The term "derived from" can mean an amino acid sequence which is a derivative or a modification of an amino acid sequence that is present in, or forms, the C-terminus of AChE, and portions thereof, or a cyclated variant thereof, such as NBP-14.

The term "truncation thereof" can mean the peptide derived from AChE is reduced in size by the removal of amino acids. The reduction of amino acids may be achieved by removal of residues from the C- or N-terminal of the peptide, or may be achieved by deletion of one or more amino acids from within the core of the peptide.

In one embodiment, the peptide, derivative or analogue thereof of the first aspect may be cyclic or cyclated. However, it is most preferred that the peptide, derivative or analogue thereof is not cyclic or cyclated. Preferably, the peptide, derivative or analogue thereof is linear. Preferably, the peptide, derivative or analogue thereof is purified and/or isolated, i.e. it is not found in nature. Preferably, the peptide, derivative or analogue thereof is at least 95% pure, or at least 99% pure, i.e. free from impurities.

Acetylcholinesterase is a serine protease that hydrolyses acetylcholine, and will be well-known to the skilled person. The major form of acetylcholinesterase which is found in the brain is known as tailed acetylcholinesterase (T-AChE). Given that the invention is primarily concerned with treating neurodegenerative disorders, it is preferred that the peptide, derivative or analogue thereof comprises or consists of an amino acid sequence derived from the C-terminus of tailed acetylcholinesterase (T-AChE), or a cyclic variant or truncation thereof.

The protein sequence of one embodiment of human tailed acetylcholinesterase (Gen Bank: AAA68151.1) is 614 amino acids in length, and is provided herein as SEQ ID No:157, as follows:

[SEQ ID No: 157]

| | | | | | |
|---|---|---|---|---|---|
| 1 | mrppqcllht | pslaspllll | llwllgggvg | aegredaell | vtvrggrlrg irlktpggpv |
| 61 | saflgipfae | ppmgprrflp | pepkqpwsgv | vdattfqsvc | yqyvdtlypg fegtemwnpn |
| 121 | relsedclyl | nvwtpyprpt | sptpvlvwiy | gggfysgass | ldvydgrflv qaertvlvsm |
| 181 | nyrvgafgfl | alpgsreapg | nvglldqrla | lqwvqenvaa | fggdptsvtl fgesagaasv |
| 241 | gmhllsppsr | glfhravlqs | gapngpwatv | gmgearrrat | qlahlvgcpp ggtggndtel |
| 301 | vaclrtrpaq | vlvnhewhvl | pqesvfrfsf | vpvvdgdfls | dtpealinag dfhglqvlvg |
| 361 | vvkdegsyfl | vygapgfskd | neslisraef | lagvrvgvpq | vsdlaaeavv lhytdwlhpe |
| 421 | dparlreals | dvvgdhnvvc | pvaqlagrla | aqgarvyayv | fehrastlsw plwmgvphgy |
| 481 | eiefifgipl | dpsrnytaee | kifaqrlmry | wanfartgdp | neprdpkapq wppytagaqq |

```
541  yvsldlrple vrrglraqac afwnrflpkl lsatdtldea erqwkaefhr wssymvhwkn 601  qfdhyskqdr csdl
```

It will be appreciated that the first 31 amino acid residues of SEQ ID No:157 are removed while the protein is released, thereby leaving a 583 amino acid sequence. Accordingly, it is preferred that the peptide, derivative or analogue thereof comprises an amino acid sequence derived from the C-terminus of acetylcholinesterase, or a cyclic variant or a truncation thereof, wherein the acetylcholinesterase comprises an amino acid sequence substantially as set out in SEQ ID No:157, or a functional variant or fragment thereof. Preferably, the 31 amino acids at the N-terminal are excluded.

Preferably, the peptide, derivative or analogue thereof comprises or consists of an amino acid sequence derived from the last 300, 200, 100 or 50 amino acids forming the C-terminus of acetylcholinesterase, or a cyclic variant or truncation thereof, most preferably wherein the acetylcholinesterase comprises an amino acid sequence substantially as set out in SEQ ID No:157. The peptide, derivative or analogue thereof preferably comprises or consists of an amino acid sequence derived from the last 40 or 30 amino acids forming the C-terminus of acetylcholinesterase, or a cyclic variant or a truncation thereof.

As described in the Examples, and as shown graphically in FIG. 7, the inventors devised a set of criteria by which active peptides are determined. The first criterion used to establish active peptides was that the value coefficient, (x), which is a measure of AChE activity and PC12 cell viability, is 1.0 to 1.1. Another criterion used was that the active peptide was 5-8 amino acids in length, since compounds of greater size are believed to have less likelihood of gaining access to the brain from the periphery, i.e. cross the blood-brain barrier.

Another criterion used to determine active peptides was based on the theoretical binding value of the peptide to the allosteric site of the α7 nicotinic-receptor. The theoretical binding value can be calculated by using the algorithm published by Trott and Olson (Ref: O. Trott, A. J. Olson, AutoDock Vina: improving the speed and accuracy of docking with a new scoring function, efficient optimization and multithreading, Journal of Computational Chemistry 31 (2010) 455-461). Hence, preferably the peptide, derivative or analogue thereof has a theoretical binding affinity to the allosteric site of the α7 nicotinic-receptor of less than to −7.0 kcal·mol$^{-1}$, more preferably less than −7.1 kcal·mol$^{-1}$, and most preferably less than −7.8 kcal·mol$^{-1}$.

A final criterion used to determine active peptides is the amount of calcium influx into PC12 cells caused by the peptide. The calcium influx value can be calculated as described in the methods section. The calcium value corresponds to the result from the experiment when applying T30 or Aβ alone or in conjunction with the small peptides. The control value for these experiments is based on the calcium influx induced by acetylcholine alone. Preferably, the peptide, derivative or analogue thereof has a calcium influx value of less than 120, and more preferably a value of 97-120.

Preferably, the peptide, derivative or analogue thereof consists of a sequence of 5 to 8 amino acids which are derived from the C-terminus of acetylcholinesterase (AChE), or a cyclic variant thereof.

It is especially preferred therefore that the peptide, derivative or analogue thereof is: (i) 5-8 amino acids in length; (ii) has a value coefficient, x, of 1.0 to 1.1; (ii) has a theoretical binding value of the peptide to the allosteric site of the α7 nicotinic-receptor of less than −7.0; and has a calcium influx value of less than 120.

In a most preferred embodiment, the peptide, derivative or analogue thereof is: (i) 5-8 amino acids in length; (ii) has a value coefficient, x, of 1.0 to 1.1; (ii) has a theoretical binding value of the peptide to the allosteric site of the α7 nicotinic-receptor of less than −7.1 or less than −7.80; and has a calcium influx value of 97 to 120.

Advantageously, and preferably, the peptide, derivative or analogue thereof of the invention is protective against the toxic effects of T30 peptide and/or Aβ. More preferably, the peptide, derivative or analogue thereof of the invention is protective against the toxic effects of T30 peptide and Aβ. The parameters of toxicity are quantified as an increase of acetylcholinesterase, decrease in cell viability, increase in calcium influx and decrease of theoretical affinity for the α7 nicotinic receptor. Changes in these parameters will determine the protective effects of the peptides.

The molecular weight of the peptide, derivative or analogue thereof of the invention is preferably less than 1000 Da, more preferably less than 900 Da.

Preferably, the peptide, derivative or analogue thereof comprises or consists of 5 and 8 amino acid residues, or 5 and 7 amino acids, or 6 and 8 amino acids.

In one preferred embodiment, the peptide, derivative or analogue thereof comprises or consists of six amino acids. Preferably, the peptide, derivative or analogue thereof comprises or consists of an amino acid sequence substantially as set out in SEQ ID No: 30, 32, 40 or 42.

The amino acid sequence of SEQ ID No: 30 (i.e. "NBP-601") is: HWKAEF.

The amino acid sequence of SEQ ID No: 32 (i.e. "NBP-603") is: KAEFHR.

The amino acid sequence of SEQ ID No: 40 (i.e. "NBP-611") is: SYMVHW.

The amino acid sequence of SEQ ID No: 42 (i.e. "NBP-613") is: MVHWKA.

Preferably, SEQ ID No: 40 is protective against the toxic effects of Aβ. Preferably, SEQ ID No's: 30, 32 and 42 are protective against the toxic effects of T30.

In another preferred embodiment, the peptide, derivative or analogue thereof comprises or consists of seven amino acids. Preferably, the peptide, derivative or analogue thereof comprises or consists of an amino acid sequence substantially as set out in SEQ ID No: 48, 51 or 53.

The amino acid sequence of SEQ ID No: 48 (i.e. "NBP-705") is: EFHRWSS.

The amino acid sequence of SEQ ID No: 51 (i.e. "NBP-708") is: RWSSYMV.

The amino acid sequence of SEQ ID No: 53 (i.e. "NBP-710") is: SSYMVHW.

Preferably, SEQ ID No: 53 is protective against the toxic effects of Aβ. Preferably, SEQ ID No's: 48 and 51 are protective against the toxic effects of T30.

In another preferred embodiment, the peptide, derivative or analogue thereof comprises or consists of eight amino acids. Preferably, the peptide, derivative or analogue thereof comprises or consists of an amino acid sequence substantially as set out in SEQ ID No: 61.

The amino acid sequence of SEQ ID No: 61 (i.e. "NBP-804") is: AEFHRWSS.

Preferably, SEQ ID No: 61 is protective against the toxic effects of T30.

It will be understood that NPB-601, 603, and 804 are all derived from cyclic NBP-14 (SEQ ID No:1), as shown in FIG. 3, in which the terminal alanine and lysine are cyclated together. NPB-601, 603, and 804 are all linear peptides and include the alanine and lysine amino acids (i.e. defining the point at which NBP-14 is ligated) connected together.

It will be appreciated that Aβ is currently the more commonly accepted mechanism of toxicity for causing neurodegenerative disorders, such as Alzheimer's disease. Accordingly, any peptide, derivative or analogue thereof according to the invention which is protective against Aβ toxicity is preferred, and therefore especially useful for treating neurodegenerative disorders. However, the inventor's previous work suggests that T30 toxicity is in fact the more likely cause for neurodegenerative diseases, and not Aβ toxicity. Accordingly, any peptide according to the invention which is protective against T30 toxicity is most preferred, and is particularly useful for treating neurodegenerative disorders.

The inventors conducted dose-dependent response experiments for the preferred linear peptides in PC12 against T30 and amyloid (Example 6). They also tested the effect of T30 on responses evoked in the basal forebrain and examined whether cyclic NBP14 or any of the shorter linear variants of the first aspect are able to reverse any T30-induced changes. Examples 6 and 7 show that NBP601, NBP603 and NBP613 protect against T30 effects. Accordingly, these peptides are the most preferred.

In a fifth aspect, there is provided a peptide, derivative or analogue thereof consisting of an amino acid sequence substantially as set out in SEQ ID No: 30, 32, 40, 42, 48, 51, 53 or 61.

In a sixth aspect of the invention, there is provided one or more peptide, derivative or analogue thereof according to the fifth aspect, for use in therapy or diagnosis.

In a seventh aspect, there is provided one or more peptide, derivative or analogue thereof according to the fifth aspect, for use in treating, ameliorating or preventing a neurodegenerative disorder.

In an eighth aspect, there is provided a method of treating, ameliorating or preventing a neurodegenerative disorder in a subject, the method comprising, administering to a subject in need of such treatment, a therapeutically effective amount of one or more peptide, derivative or analogue thereof according to the fifth aspect.

In a preferred embodiment, a single peptide, derivative or analogue thereof is used for treating the neurodegenerative disease. However, based on the results, in another embodiment, more than one peptide, derivative or analogue thereof is used for treating the neurodegenerative disease, i.e. in a combination therapy. For example, a plurality of peptides which have been shown to be protective against Aβ toxicity may be used. Alternatively, preferably a plurality of peptides which have been shown to be protective against T30 toxicity can be used.

In a preferred embodiment, however, one or more peptide which is protective against T30 toxicity is used in combination with one or more peptide which is protective against Aβ toxicity, i.e. administration of two peptides, one from the T30 protective group shown in Table 1 and one from the Aβ protective group shown in Table 2. For example, NBP-601 (SEQ ID No:30) may be co-administered with NBP-710 (SEQ ID No: 53), or NBP-804 (SEQ ID No: 61) may be co-administered with NBP-611 (SEQ ID No: 40), and so on.

It will be appreciated that peptides according to the invention may be used in a medicament which may be used in a monotherapy (i.e. use of the one or more peptide, derivative or analogue thereof of the first aspect), for treating, ameliorating, or preventing neurodegenerative disorder, such as Alzheimer's disease. Alternatively, the peptide according to the invention may be used as an adjunct to, or in combination with, known therapies for treating, ameliorating, or preventing Alzheimer's disease, such as acetylcholinesterase inhibitors.

The peptides according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the peptide across the blood-brain barrier.

It will be appreciated that the efficiency of any treatment for brain disorders depends on the ability of the candidate therapeutic peptide to cross the blood-brain barrier (BBB). However, it is well-known that, during Alzheimer's disease, the blood-brain barrier increases in permeability that could allow the peptides of the invention to reach the central nervous system, indeed ideally only at the sites of degeneration where it is needed, i.e. where the BBB is compromised.

Two main strategies may be applied to cross the BBB with peptides of the invention, including: (1) use of nanoparticles as transporters to specifically target the brain and deliver the active compound. This method has successfully been used to deliver peptides, proteins and anticancer drugs deliver to the brain; (2) use of cargo peptides. The addition of such a peptide specifically transported across the BBB allows the transfer of the peptides of the invention through a facilitated manner.

Medicaments comprising polypeptides according to the invention may be used in a number of ways. For instance, oral administration may be required, in which case the polypeptide may be contained within a composition that may, for example, be ingested orally in the form of a tablet, capsule or liquid. An alternative option for administrating the peptides would be to use a nasal spray, since peptide administration by nasal spray reaches the brain faster and more efficiently than oral or intravenous ways of administration (see http://memoryzine.com/2010/07/26/nose-sprays-cross-blood-brain-barrier-faster-and-safer/). Hence, compositions comprising polypeptides of the invention may be administered by inhalation (e.g. intranasally). Compositions may also be formulated for topical use. For instance, creams or ointments may be applied to the skin, for example, adjacent the brain.

Polypeptides according to the invention may also be incorporated within a slow- or delayed-release device. Such devices may, for example, be inserted on or under the skin, and the medicament may be released over weeks or even months. The device may be located at least adjacent the treatment site, e.g. the head. Such devices may be particularly advantageous when long-term treatment with polypeptides used according to the invention is required and which would normally require frequent administration (e.g. at least daily injection).

In a preferred embodiment, medicaments according to the invention may be administered to a subject by injection into the blood stream or directly into a site requiring treatment. For example, the medicament may be injected at least adjacent the brain. Injections may be intravenous (bolus or infusion) or subcutaneous (bolus or infusion), or intradermal (bolus or infusion).

It will be appreciated that the amount of the polypeptide that is required is determined by its biological activity and bioavailability, which in turn depends on the mode of administration, the physiochemical properties of the polypeptide and whether it is being used as a monotherapy or in a combined therapy. The frequency of administration will also be influenced by the half-life of the polypeptide within the subject being treated. Optimal dosages to be administered may be determined by those skilled in the art, and will vary with the particular polypeptide in use, the strength of the pharmaceutical composition, the mode of administration, and the advancement of the neurodegenerative disease. Additional factors depending on the particular subject being treated will result in a need to adjust dosages, including subject age, weight, gender, diet, and time of administration.

Generally, a daily dose of between 0.001 µg/kg of body weight and 10 mg/kg of body weight of the polypeptide according to the invention may be used for treating, ameliorating, or preventing neurodegenerative disease, depending upon which polypeptide is used. More preferably, the daily dose is between 0.01 µg/kg of body weight and 1 mg/kg of body weight, and most preferably between approximately 0.1 µg/kg and 10 µg/kg body weight.

The polypeptide may be administered before, during or after onset of neurodegenerative disease. Daily doses may be given as a single administration (e.g. a single daily injection or inhalation of a nasal spray). Alternatively, the polypeptide may require administration twice or more times during a day. As an example, polypeptides may be administered as two (or more depending upon the severity of the neurodegenerative disease being treated) daily doses of between 0.07 µg and 700 mg (i.e. assuming a body weight of 70 kg). A patient receiving treatment may take a first dose upon waking and then a second dose in the evening (if on a two dose regime) or at 3- or 4-hourly intervals thereafter. Alternatively, a slow release device may be used to provide optimal doses of polypeptide according to the invention to a patient without the need to administer repeated doses.

Known procedures, such as those conventionally employed by the pharmaceutical industry (e.g. in vivo experimentation, clinical trials, etc.), may be used to form specific formulations of the polypeptide according to the invention and precise therapeutic regimes (such as daily doses of the agents and the frequency of administration). The inventors believe that they are the first to suggest an anti-neurodegenerative disease composition, based on the use of a polypeptide of the invention.

Hence, in a fifth aspect of the invention, there is provided a pharmaceutical composition comprising a therapeutically effective amount of one or more peptide, derivative or analogue thereof according to the first aspect, and optionally a pharmaceutically acceptable vehicle.

The pharmaceutical composition is preferably an anti-neurodegenerative disease composition, i.e. a pharmaceutical formulation used in the therapeutic amelioration, prevention or treatment of a neurodegenerative disorder in a subject, such as Alzheimer's disease.

The invention also provides in a sixth aspect, a process for making the pharmaceutical composition according to the fifth aspect, the process comprising combining a therapeutically effective amount of the peptide, derivative or analogue thereof according to the first aspect, with a pharmaceutically acceptable vehicle.

The peptide, derivative or analogue thereof is preferably NBP-601 (SEQ ID No:30), NBP-603 (SEQ ID No:32), NBP-613 (SEQ ID No:42), NBP-705 (SEQ ID No:48), NBP-708 (SEQ ID No:51), NBP-804 (SEQ ID No:61), NBP-611 (SEQ ID No:40) or NBP-710 (SEQ ID No:53).

A "subject" may be a vertebrate, mammal, or domestic animal. Hence, medicaments according to the invention may be used to treat any mammal, for example livestock (e.g. a horse), pets, or may be used in other veterinary applications. Most preferably, however, the subject is a human being.

A "therapeutically effective amount" of peptide is any amount which, when administered to a subject, is the amount of active agent that is needed to treat the neurodegenerative disorder condition, or produce the desired effect.

For example, the therapeutically effective amount of peptide used may be from about 0.001 mg to about 800 mg, and preferably from about 0.01 mg to about 500 mg. It is preferred that the amount of peptide is an amount from about 0.1 mg to about 100 mg.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, coatings, or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The polypeptide may be prepared as a sterile solid composition that may be dissolved or suspended at the time of administration using sterile water, saline, or other appropriate sterile injectable medium.

The polypeptide and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The polypeptide used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequence identified as SEQ ID No:1-157, and so on.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=-1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to DNA sequences or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences described herein.

Due to the degeneracy of the genetic code, it is clear that any nucleic acid sequence described herein could be varied or changed without substantially affecting the sequence of the protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

In a further aspect, there is provided a peptide, derivative or analogue thereof comprising a sequence of 5 to 8 amino acids which are derived from the C-terminus of acetylcholinesterase (AChE), or a truncation thereof, wherein the peptide, derivative or analogue thereof has a value coefficient, x, of 1.0 to 1.1,
wherein $$x = \frac{\% \text{ AChE release}}{\% \ PC_{12} \text{ cell viability}},$$

wherein "% AChE release" is the percentage of acetylcholinesterase released from a PC12 cell preparation cultured in the presence of the peptide, derivative or analogue thereof compared to that of the PC12 cell preparation cultured in the absence of the peptide, derivative or analogue thereof, and "% PC12 cell viability" is the percentage viability of the PC12 cell preparation cultured in the presence of the peptide, derivative or analogue thereof compared to that of a PC12 cell preparation cultured in the absence of the peptide, derivative or analogue thereof.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

FIG. 1a shows the binding of cyclic polypeptide NBP-14 (referred to herein as SEQ ID No:1) binding to the α7 nicotinic-receptor, and FIG. 1b shows an enlarged view of the 3D structure of cyclic NBP-14;

FIG. 4a-4k are tables showing various embodiments of the linear peptide according to the invention. The peptides are divided into respective groups of peptides which have four, five, six, seven, eight, nine, ten, eleven, twelve, thirteen or fourteen amino acids;

FIG. 5 is a graphical representation of the theoretical affinity of the peptides making up various embodiments of the linear peptides of the invention with the target site of the α7 nicotinic-receptor;

Figures 6, 6A:
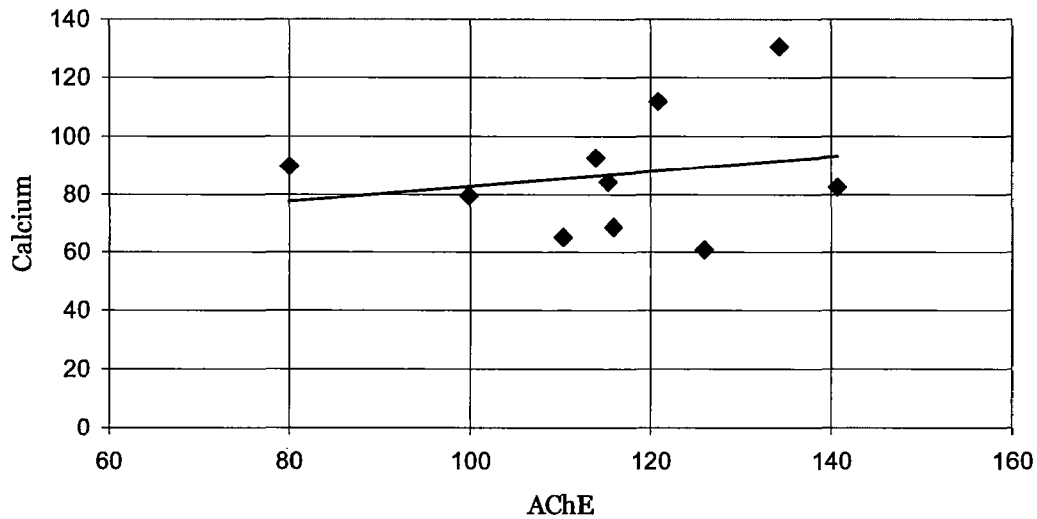
Figure 6B:
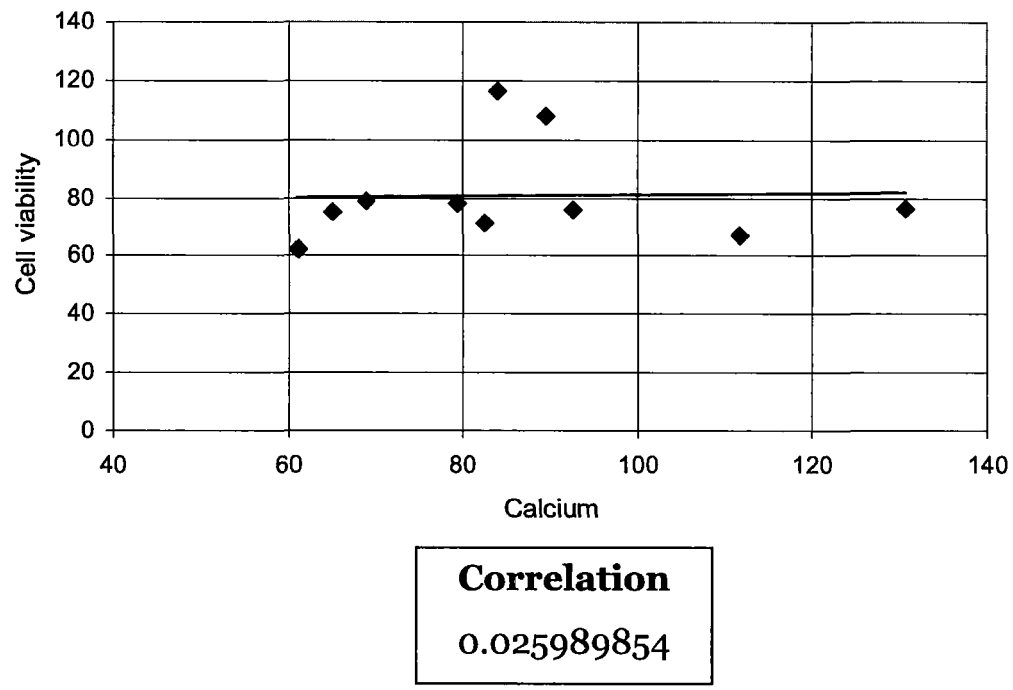
Figure 6C:
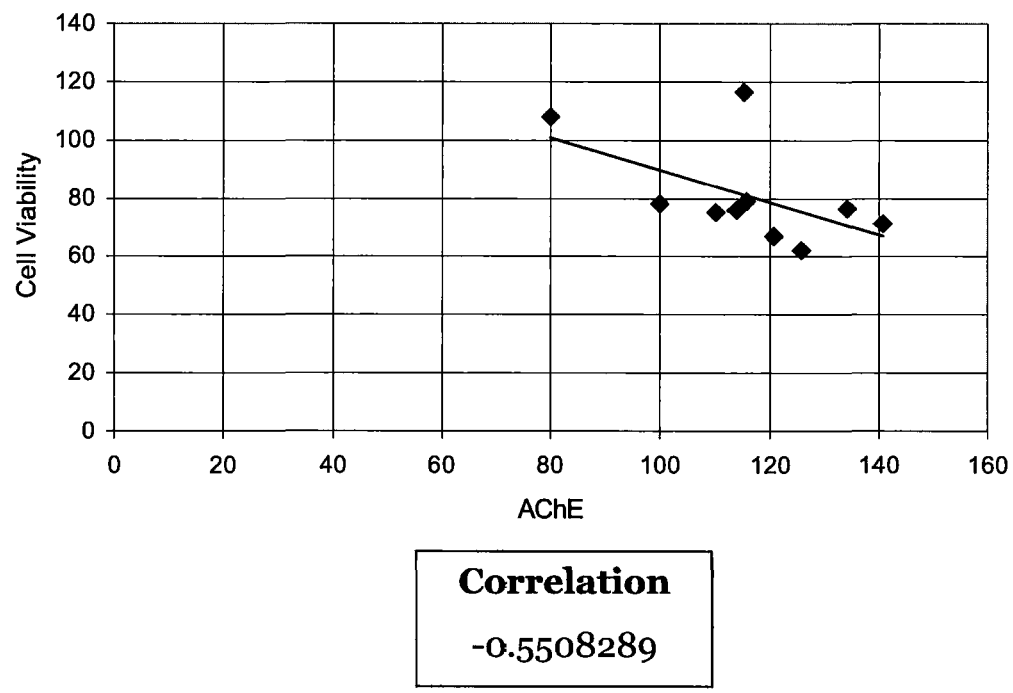
Figure 7:
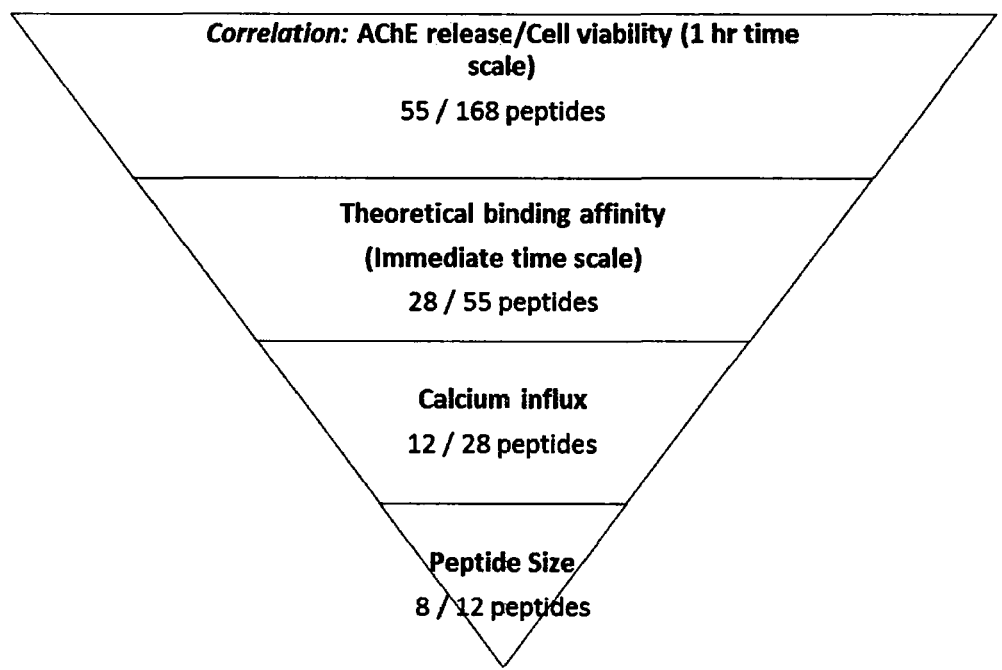
Figure 8:
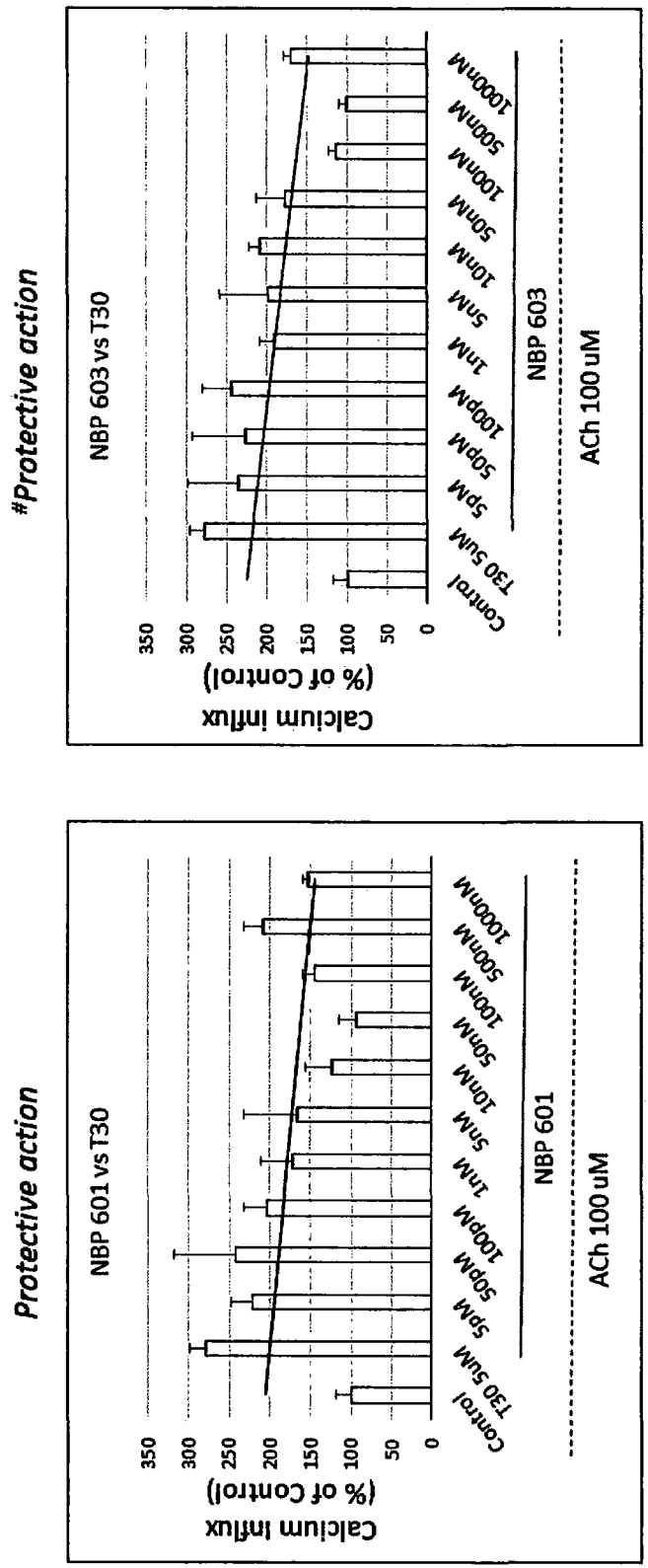
Figure 9:
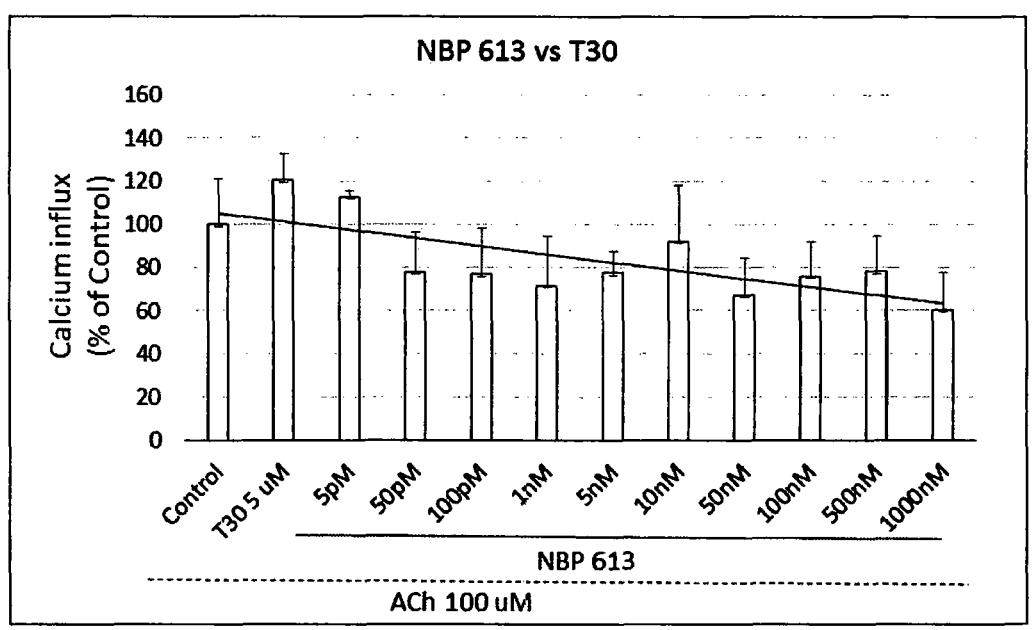

FIG. 6 shows the data and corresponding graphs showing the relationship between acetyl cholinesterase release, calcium ion influx and cell viability. FIG. 6a shows the relationship between acetyl cholinesterase release and calcium ion influx (correlation is 0.210), FIG. 6b shows the relationship between calcium ion influx and cell viability (correlation is 0.026), and FIG. 6c shows the relationship between acetyl cholinesterase release and cell viability (correlation is −0.550);

FIG. 7 is a flow chart showing the four filters or criteria used in the determination of active peptides in accordance with the invention. Criterion 1 involves the correlation between AChE release from PC12 cells and PC12 cell viability; criterion 2 involves the theoretical binding affinity of the peptides remaining following application of criterion 1; criterion 3 involves the calcium ion influx in PC12 cells caused by the peptides remaining following application of criterion 2; and criterion 4 involves peptide size, i.e. excluding peptides remaining following application of criterion 3 with more than 8 amino acids;

FIG. 8 are graphs showing the dose-dependent effects on calcium potentiation of linear variant NBP-601 or NBP-603 against T30;

FIG. 9 are graphs showing the dose-dependent effect on calcium potentiation of linear variant NBP-613 against T30

Figure 10:
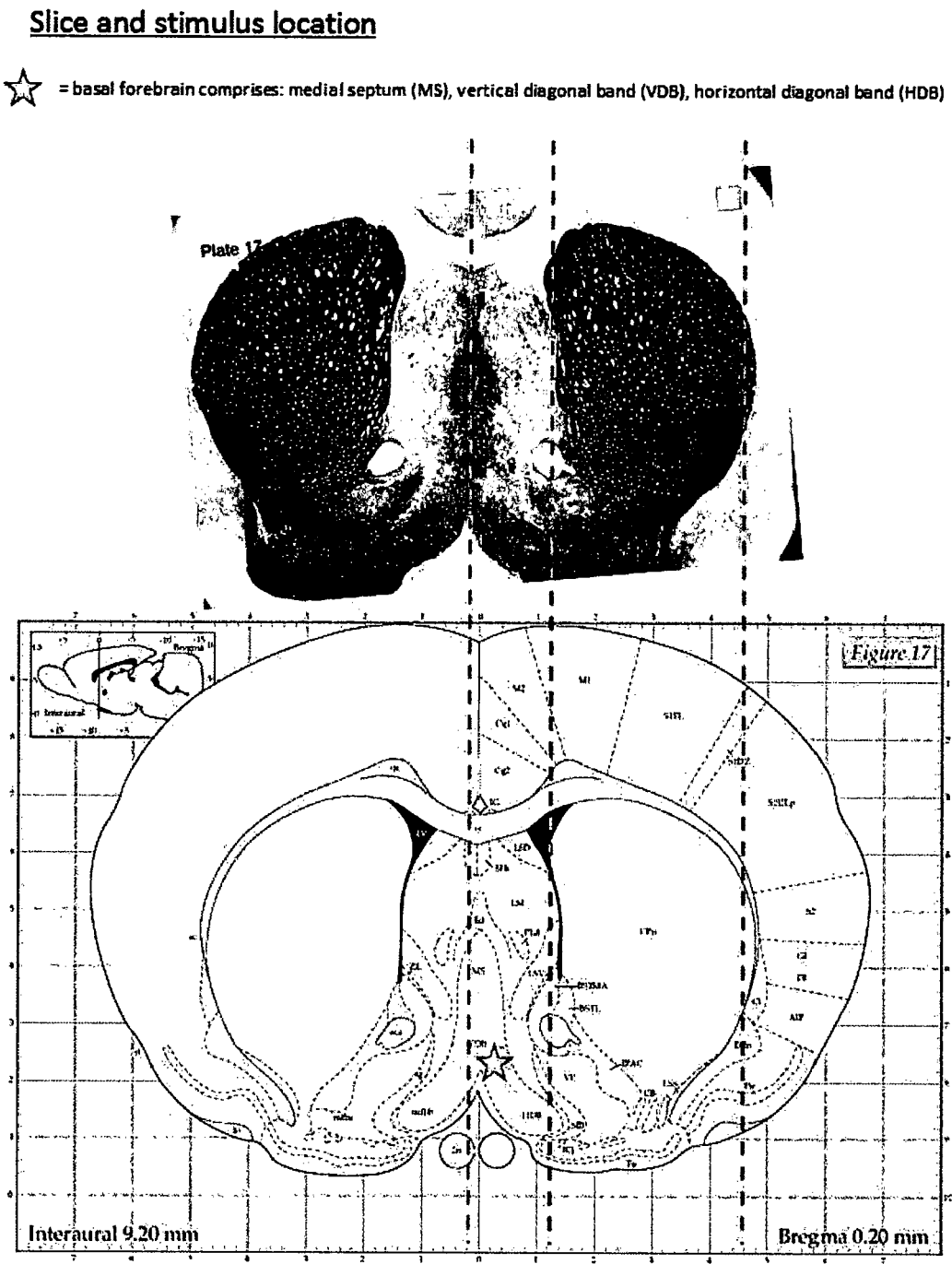
Figure 11:
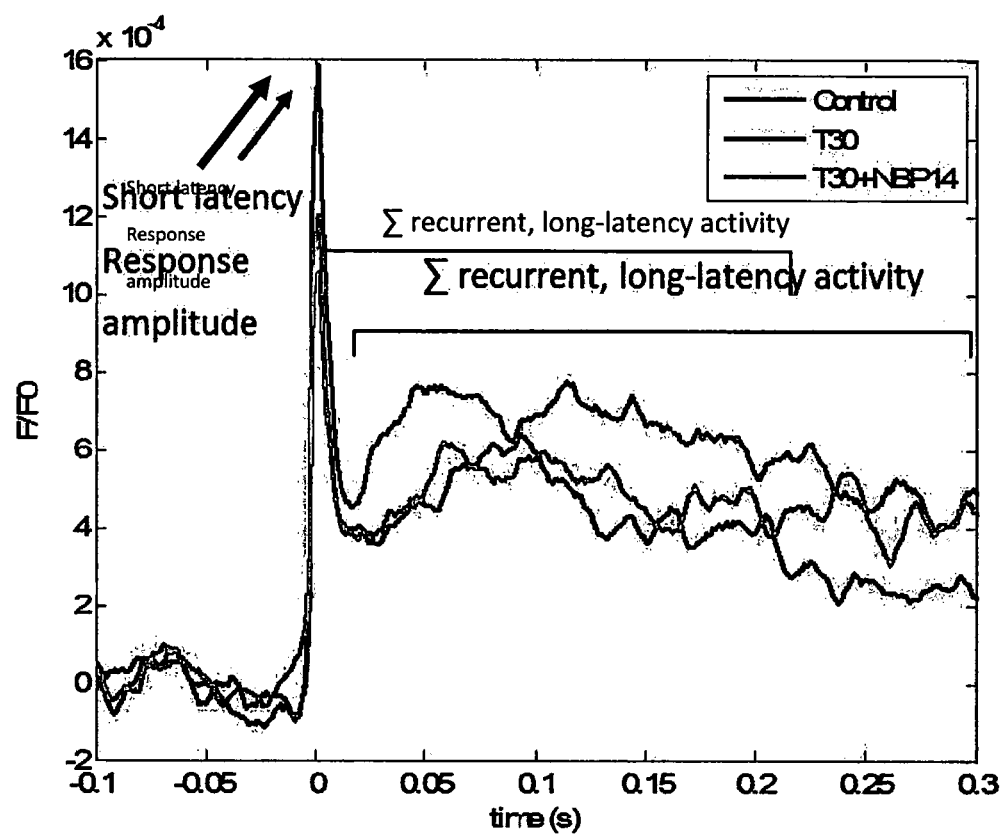
Figure 12:
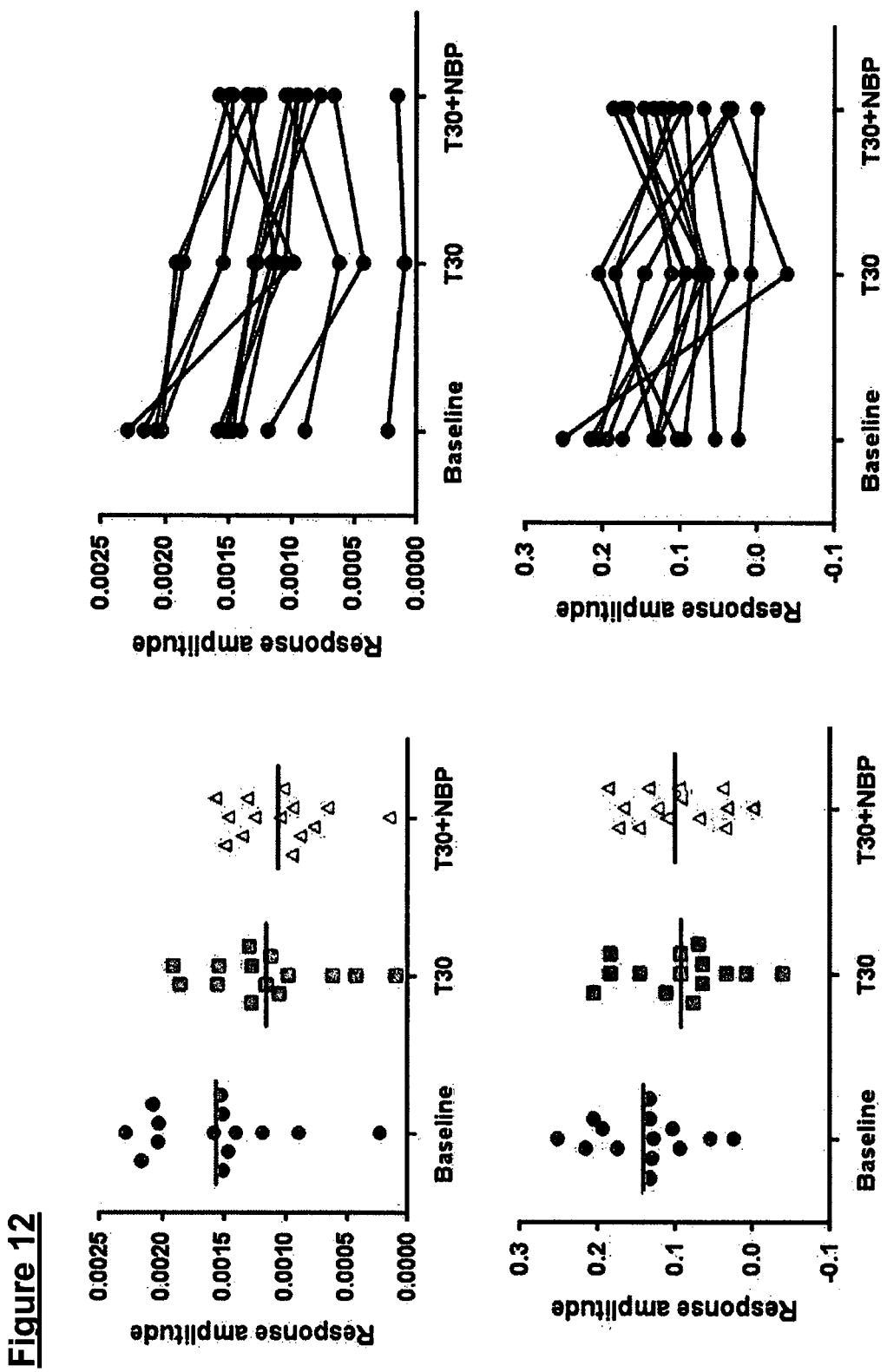
Figure 13:
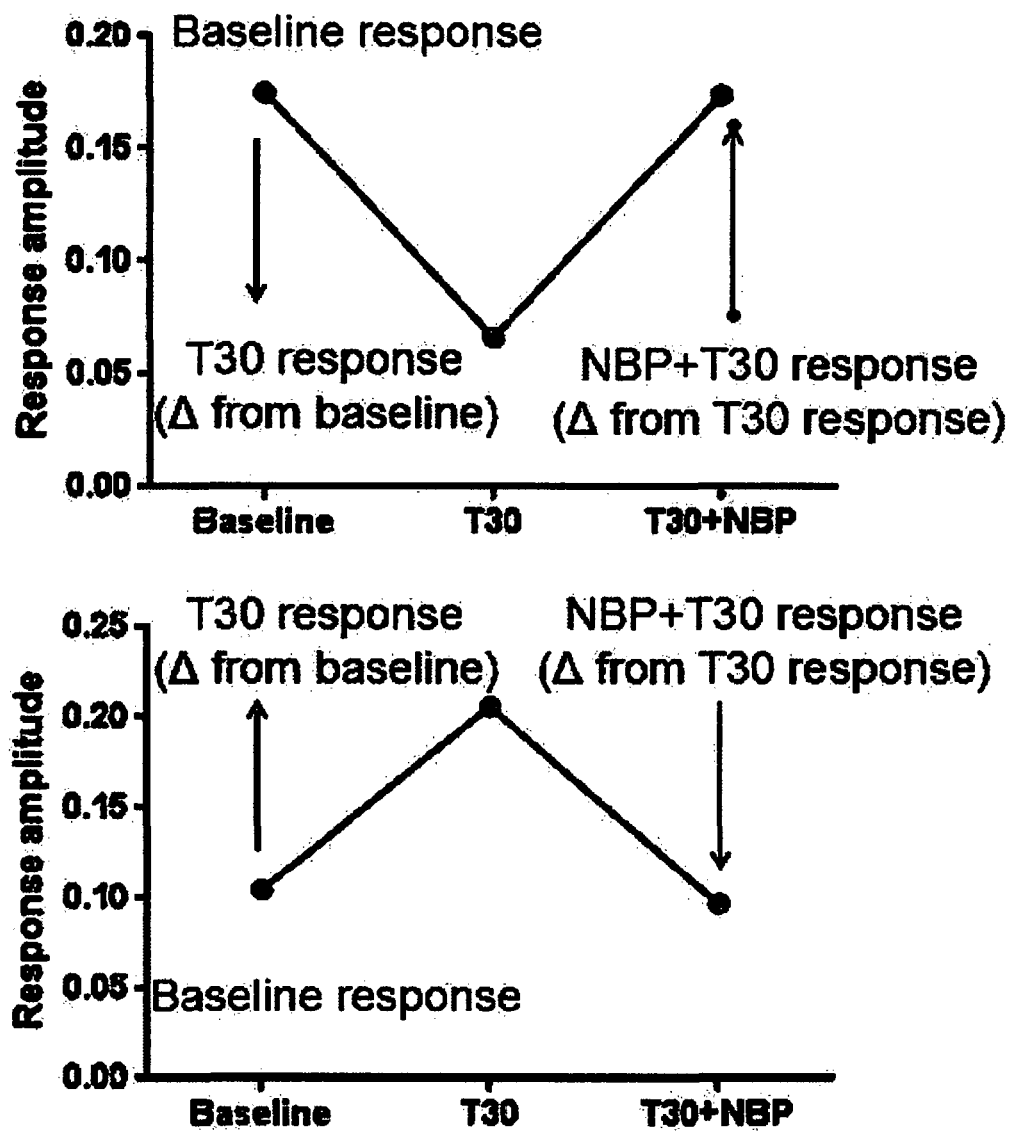
Figure 14:
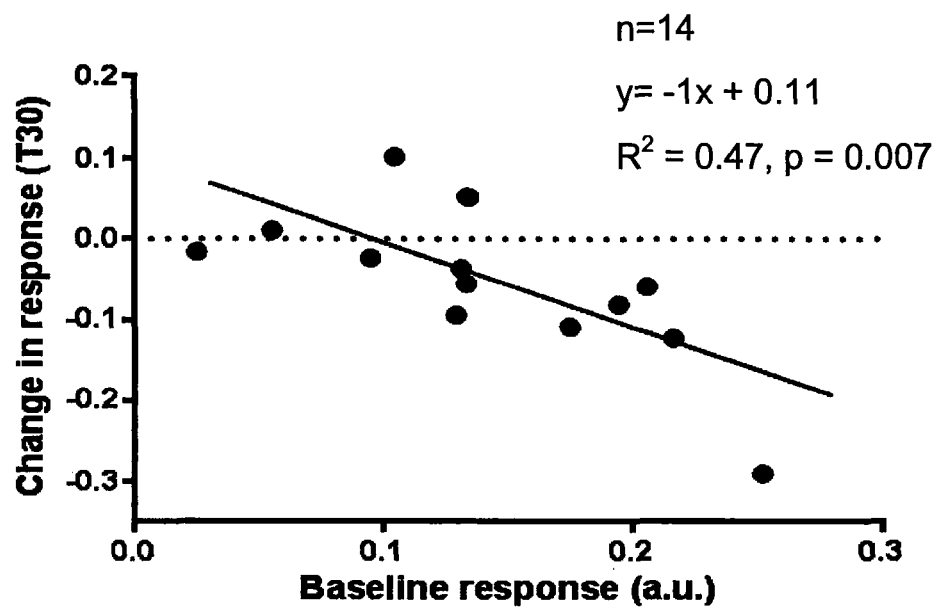
Figure 15:
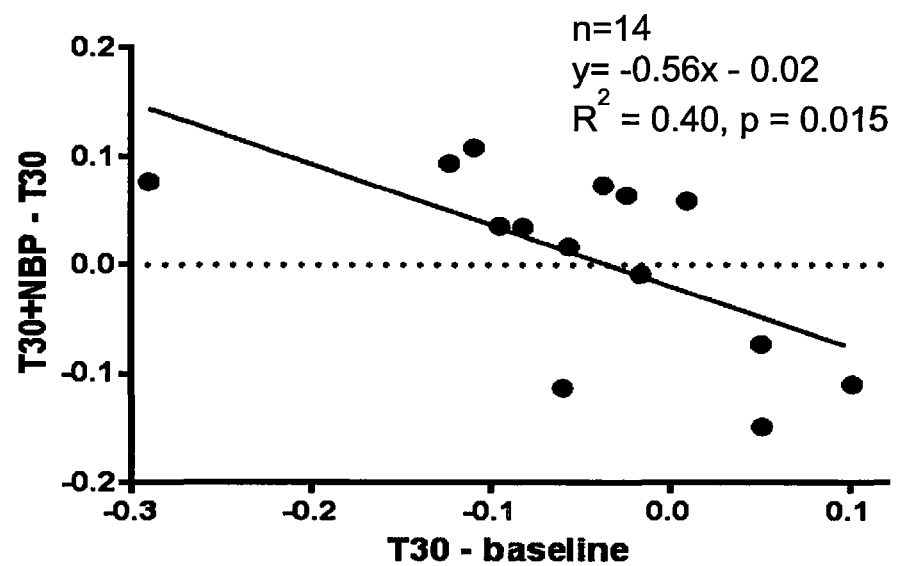
Figure 16:
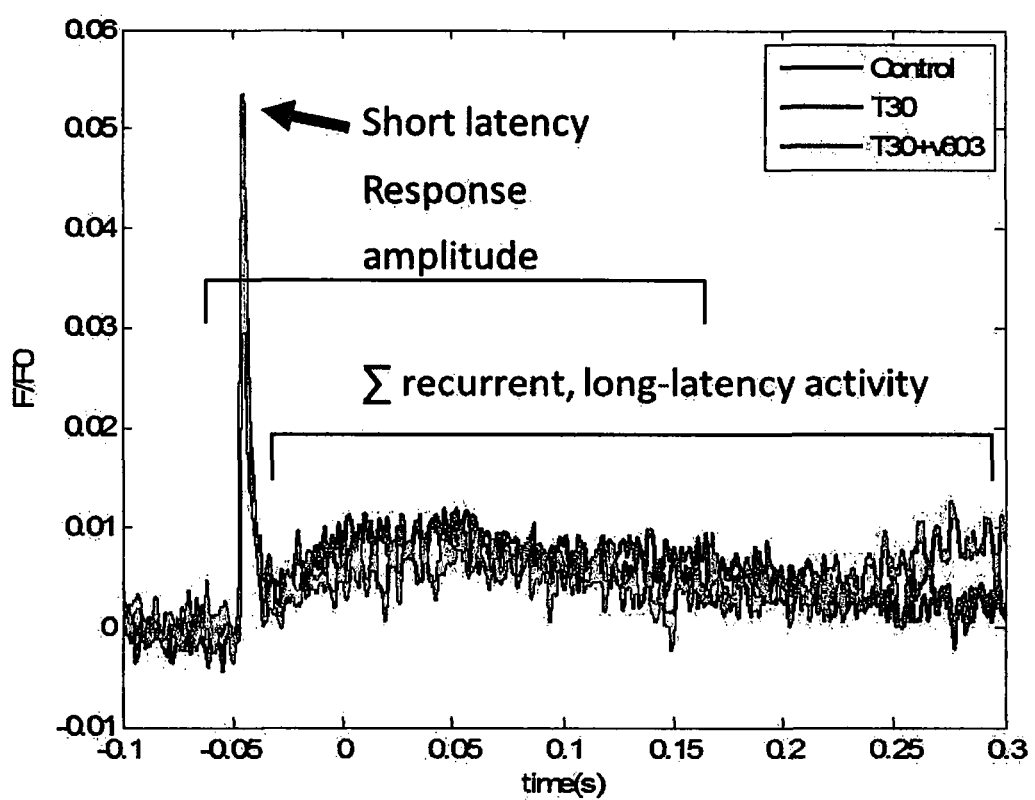
Figure 17:
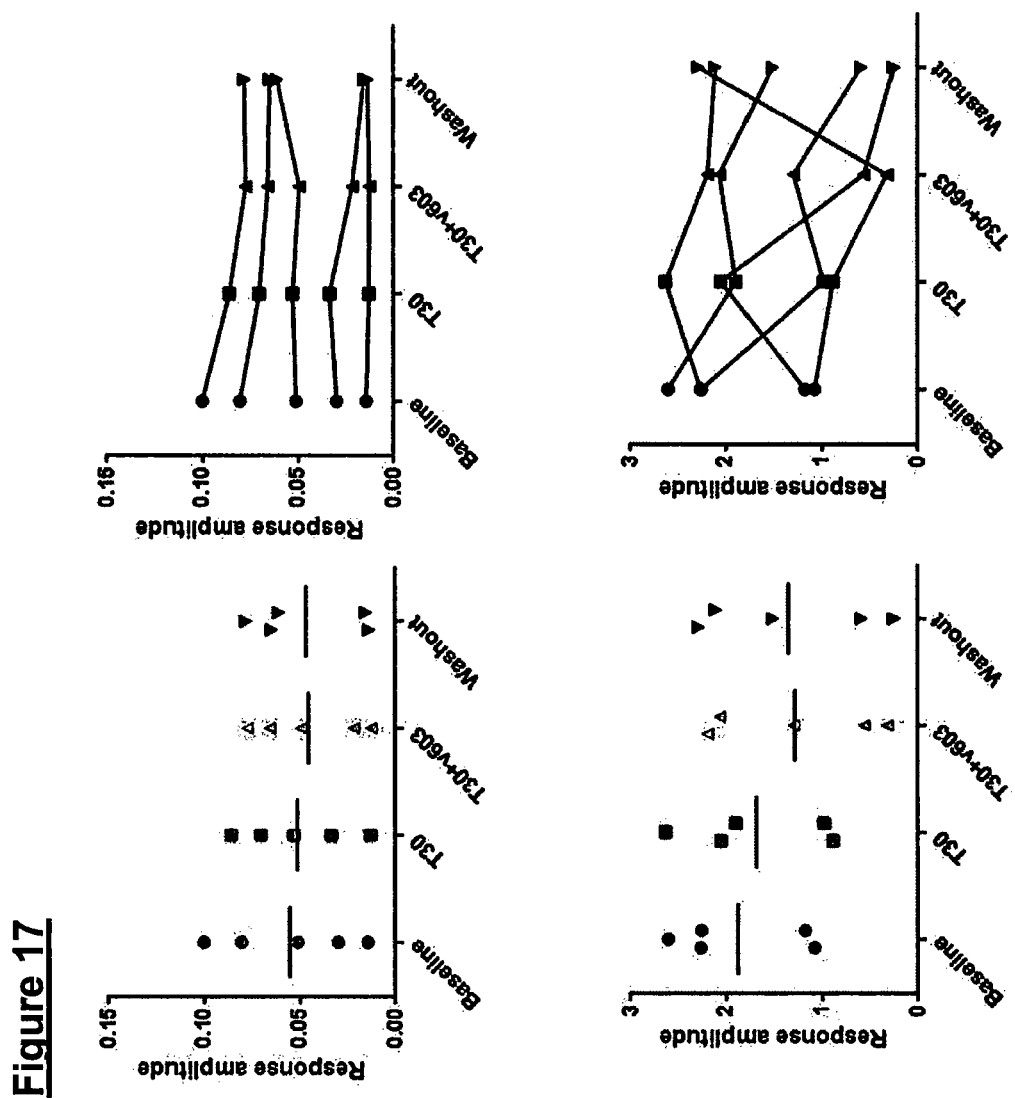
Figure 18:
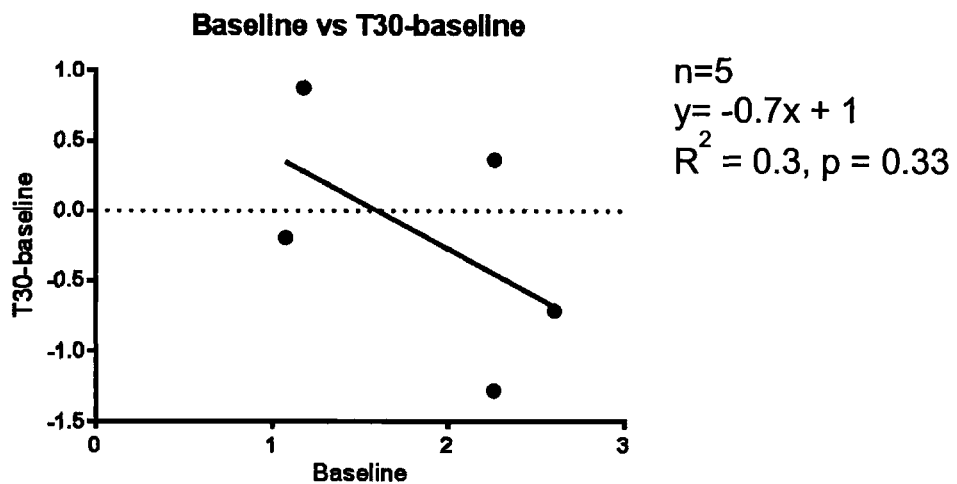
Figure 19:
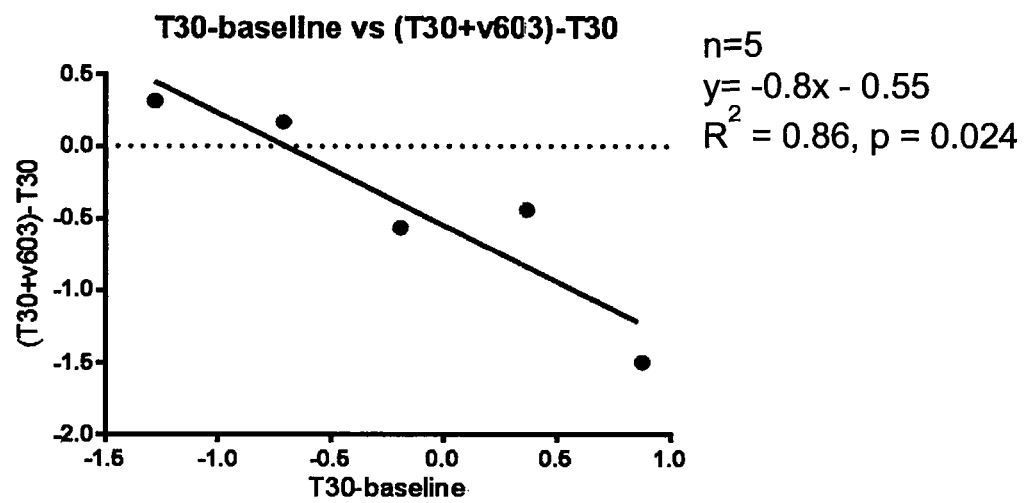
Figure 20:
Figure 21:
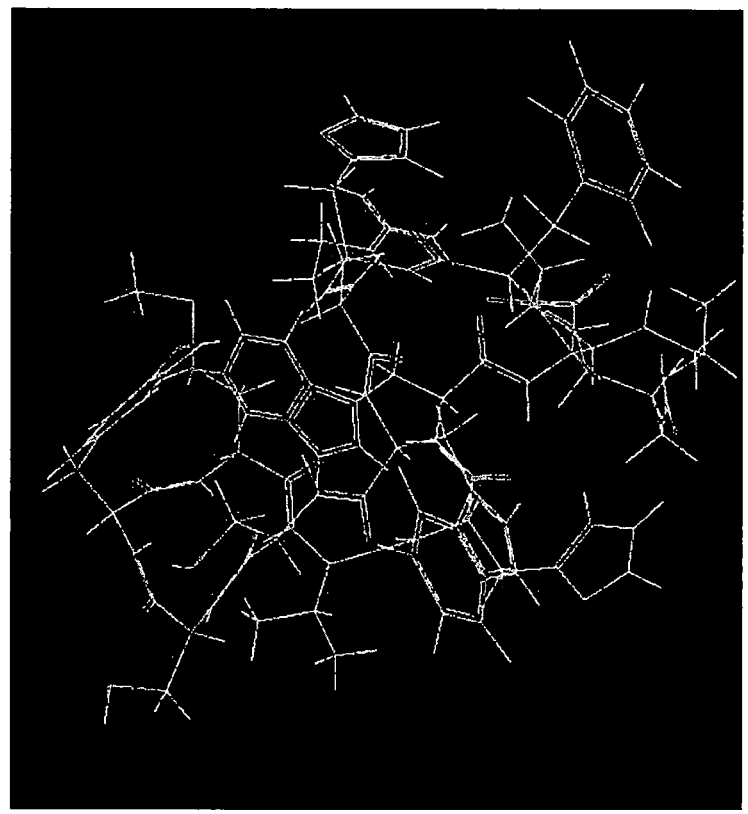

FIG. 10 is a picture (top panel) and matching schematic representation (bottom panel) of coronal rat brain slices containing diagonal band complex (medial sepctal nucleus (MS), ventral limb diagonal band (VDB), horizontal limb diagonal band (HDB); brain sub-regions which constitute part of the basal forebrain. Red stars indicate the approximate location of stimulation for voltage-sensitive dye imaging (VSDI) and electrophysiology experiments;

FIG. 11 shows VSDI averaged time-series showing the amount of fluorescence ($dF/F_0$) emitted within the region of interest (ROI) during baseline (blue trace), T30 (2 µM; green trace) and T30 (2 µM) & NBP14 (4 µM; red trace) perfusion conditions. The response profile in basal forebrain shows a tri-phasic response, with phase 1 being the initial peak response (0-15 ms after initial stimulation), phase 2 being the short period of quiescence seen directly after the peak response (15-25 ms after initial stimulation), and phase 3 seen as rebound, long-latency (recurrent) activity directly following phase 2 (25 ms+ after stimulation). Data were acquired by summing (Σ) the emitted fluorescence between 0 and 280 ms following initial stimulation;

FIG. 12 shows compiled raw data graphs (n=14) showing individual data points of maximum peak amplitude (phase 1) for baseline (blue), T30 (green) and T30 & NBP14 (red)— top left panel; individual data points of summed fluorescence ($\Sigma dF/F_0$) responses—bottom left panel. Same data showing experiment-specific trends in peak response amplitude (top right panel) and summed fluorescence (bottom right panel). Y-axis units for top panels: recorded fluorescence, $dF/F_0$; bottom panels: sum of recorded fluorescence (0→280 ms post-stimulus), $\Sigma dF/F_0$;

FIG. 13 shows individual values of summed long-latency activity taken from the raw data pool (shown in FIG. 12, bottom panels) showing example experiments where T30 induced a decrease in overall basal forebrain neuronal network activity (top panel) as well as where T30 induced an increase in network activity (bottom panel). In both cases, the change in network activity shows at least a 50% change in response (increase/decrease) from baseline level. In both cases, co-perfusion of T30 with NBP14 (third condition) always reverted the change induced by T30 perfusion back towards baseline activity level;

FIG. 14 is a graph showing individual data points of summed emitted fluorescence during baseline response (x-axis) plotted against the change induced by T30 perfusion (T30 response—baseline response; y-axis). A correlation can be seen where the higher the level of baseline response, the greater the change induced by T30 is; p=0.007;

FIG. 15 is a graph showing individual data points of change induced in summed emitted fluorescence during T30 perfusion (T30 response—baseline response; x-axis) plotted against the change induced by addition of NBP14 to the perfusate (T30 & NBP14 response—T30 response; y-axis). A correlation can be seen where the greater the change induced by T30, the greater the reversal of that effect is upon addition of NBP14; p=0.015—indicating NBP14 is an efficient blocker of T30 action;

FIG. 16 shows VSDI averaged time-series showing the amount of fluorescence (dF/F$_0$) emitted within the region of interest (ROI) during baseline (blue trace), T30 (2 µM; green trace) and T30 (2 µM) & NBP-603 (4 µM; red trace) perfusion conditions. Data were acquired by summing (Σ) the emitted fluorescence between 0 and 280 ms following initial stimulation;

FIG. 17 shows compiled raw data graphs (n=5) showing individual data points of maximum peak amplitude (phase 1) for baseline (blue), T30 (green) and T30 & NBP-603 (red)—top left panel; individual data points of summed fluorescence (ΣdF/F$_0$) responses—bottom left panel. Same data showing experiment-specific trends in peak response amplitude (top right panel) and summed fluorescence (bottom right panel). Y-axis units for top panels: recorded fluorescence, dF/F$_0$; bottom panels: sum of recorded fluorescence (0→280 ms post-stimulus), ΣdF/F$_0$;

FIG. 18 is a graph showing individual data points of summed emitted fluorescence during baseline response (x-axis) plotted against the change induced by T30 perfusion (T30 response—baseline response; y-axis). Due to the low number of data points and the high variability between them, a downward trend is found (just as seen above); p>0.05;

FIG. 19 is a graph showing individual data points of change induced in summed emitted fluorescence during T30 perfusion (T30 response—baseline response; x-axis) plotted against the change induced by addition of NBP-603 to the perfusate (T30 & NBP-603 response—T30 response; y-axis). A correlation can be seen where the more positive the change induced by T30 perfusion is, the greater the reversal of the effects once NBP-603 is added to the perfusate; p=0.024;

FIG. 20 shows the binding of linear peptide NBP-601 (referred to herein as SEQ ID No:30) binding to the α7 nicotinic-receptor (α7-nAChR); and FIG. 21 shows the chemical structure of cyclic NBP-14.

EXAMPLES

Materials and Methods
PC12 Cell Cultures

PC12 cells are a cloned, pheochromocytoma cell line derived from the adrenal medulla (Greene and Tischler, 1976, Proc Natl Acad Sci USA 73: 2424-2428; Mizrachi et al., 1990, Proc Natl Acad Sci USA 87: 6161-6165). They are easily cultured and readily accessible to experimental manipulations. Since chromaffin cells are derived from the neural crest but are located in the centre of an accessible peripheral organ (the adrenal medulla) they have been described as offering a 'window' into the brain (Bornstein et al., 2012, Mol Psychiatry 17: 354-358). These cells serve as a powerful, albeit novel, in vitro model for studying the still unknown primary process of neurodegeneration and the reasons why they are useful for this project are the following: the adrenal medulla in Alzheimer's patients shows various pathological features reminiscent of those seen in the CNS, e.g. numerous Lewy-body like inclusions, neurofibrillary tangles and paired helical filaments, as well as expression of amyloid precursor protein (APP) (Takeda et al., 1994, Neurosci Lett 168: 57-60). Moreover Appleyard and Macdonald (1991, Lancet 338: 1085-1086) demonstrated a selective reduction only in the soluble (i.e. releasable) form of AChE from the adrenal gland in AD, perhaps due to its enhanced secretion into the plasma, where it is elevated in AD patients (Atack et al., 1985, J Neurol Sci 70: 1-12; Berson et al., 2008, Brain 131: 109-119).

Wild-type PC12 cells were provided by Sigma-Aldrich (St. Louis, Mo.). The PC12 cell culture or preparation was routinely plated in 100 mm dishes (Corning) coated with collagen (2 µg/cm$^2$) and maintained in growth medium with Minimum Essential Medium Eagle (MEM) supplemented with heat-inactivated 10% horse serum (HS) and 5% foetal bovine serum (FBS), 10 mM HEPES, 2 mM L-Glutamine and 1:400 Penicillin/streptomycin solution. Cells were maintained at 37° C. in a humidified atmosphere 5% CO$_2$ and the medium was replaced every 2 days. For splitting, cells were dislodged from the dish using a pipette with medium, with a portion of these replated onto new cultured dishes. Cells were used between passages 12 and 25.

β-Amyloid Preparation

β-Amyloid (1-42) fibrils were prepared as described by provider (Abcam, Cambridge UK)). 1 mg of β-Amyloid (1-42) was dissolved in 1 ml of 100% 1,1,1,3,3,3-hexafluoro-2-propanol (HFIP). This solution was incubated at room temperature for 1 h. Next, the silution was sonicated for 10 min and then dried in a speed vacuum drier (Thermo Fisher Scientific, Loughborough, UK) and stored at −80° C. For experiments, samples were diluted in 100% DMSO and incubated for 2 h at room temperature to ensure fibril formation.

Cell Viability Assay

A Cell Counting Kit-8 (CCK-8) was used as an improvement of the SRB technique used before. By utilizing the highly water-soluble tetrazolium salt WST-8, CCK-8 produces a water-soluble formazan dye upon reduction in the presence of an electron carrier. WST-8 is reduced by dehydrogenases in cells to give a yellow colored product (formazan), which is soluble in the tissue culture medium. The amount of the formazan dye generated by the activity of dehydrogenases in cells is directly proportional to the number of living cells. PC12 cells are plated in 200 µl of complete growth medium the day before the experiment in 96 well plates. Treatments with T30 or Aβ alone or in conjunction with NBP-14 or the smaller peptides are added and incubated for 1 hour in the incubator. Subsequently, 100 µl of growth medium is removed and 10 µl of CCK-8 (Cell Counting Kit-8) solution is added. The plate is incubated for 2 hours in the incubator and then placed in the absorbance plate reader. The absorbance must be measured at 450 nm.

Acetylcholinesterase Activity Assay

AChE activity was measured using the Ellman reagent that measures the presence of thiol groups as a result of AChE activity. Cells were plated the day before the experiment as for the cell viability assay. Cells were treated with T30 or Aβ (5 µM) alone or combined with NBP-14 or the small peptides (0.5 µM). After treatment, supernatant (perfusate) of each treatment was collected and 25 µL of each condition were added to a new flat bottomed 96 well plate followed by the addition of 175 µl of Ellman reagent (Solution A: KH$_2$PO$_4$ 139 mM and K$_2$HPO$_4$ 79.66 mM, pH 7.0; solution B (substrate): Acetylthiocholine Iodide 11.5 mM; Solution C (Reagent): 5, 5'-Dithiobis (2-nitrobenzoic acid) 8 mM and NaHCO$_3$ 15 mM). The Ellman reagent was prepared as a mixture of the 3 solutions in a ratio 33(A):3(B):4(C). Absorbance measurements were taken at regular intervals (3, 10, 30 and 60 mins) across experiments at 405 nm.

Calcium Fluorometry

PC12 cells are plated in 200 μl of complete growth medium the day before the experiment in 96 well plates. On the day of the experiment, the Fluo-8 solution (Abcam) is prepared (as per provider protocol). Subsequently, 100 μl of growth medium is removed and 100 μl of Fluo-8 solution is added. Treatments with T30 or Aβ in conjunction with NBP-14 or small peptides are added and incubated for 30 minutes in the incubator and 30 minutes room temperature.

After 1 hour, the plate is placed in the fluorescence plate reader (Fluostar). Before reading the fluorescence, acetylcholine (ACh) 100 μM is prepared and placed in the Fluostar injector. For each well, the reading will be formed by a basal fluorescence followed by acetylcholine injection that will induce an increase of calcium via nicotinic receptors. The effects of the peptides are then evaluated.

VSDI Methodology:

Preparation of Brain Slices and Ex-Vivo Recordings

Coronal rat brain slices were prepared according to the procedure described in (Badin et al., 2013) but this time containing basal forebrain (+0.70 and −0.26 millimetres (mm) from bregma (Paxinos and Watson, 1998). Optical imaging using voltage-sensitive dyes was then performed as previously described (Badin et al., 2013, *Neuropharmacology.* 73C:10-18).

Data Analysis and Statistics (VSDI)

VSDI data were recorded in 4×4 mm 2-dimensional images, equivalent to 100×100 pixels—each pixel being 40×40 micrometres (μm), from which critical data were extracted. VSDI data was not gathered throughout the experimental run, but in fact was recorded in discrete periods of time 15 minutes in length. The inter-stimulus interval (ISI) between stimulations was 28 seconds and therefore, every recording epoch consisted of 32 successive stimulations. The data from all 32 stimulations were then averaged into a single file for each experimental condition and analysed using a VSDI data analysis toolbox specially made for MatLab (Bourgeois et al., 2014, PLoS One. 9:e108686). In short, this toolbox allowed for the selection of a fixed region of interest (ROI) geometry which could be applied to every slice, in order to extract and compound the data from an identical ROI across all slices and experimental conditions. The ROI was selected along the pial surface of the septal region of slices to encompass the medial septal nucleus (MS), the ventral limb of the diagonal band (VDB) and the horizontal limb of the diagonal band (HDB). VSDI data, taken from the ROI, was then plotted as a single averaged time series (FIG. 11). In order to quantify VSDI data however, the area under the curve was calculated (summed fluorescence fractional change, FIG. 11-22) between the moment of stimulation (t=0) and 280 ms after that; this method of quantification takes into account all the components of the immediate and longer-latency response. All statistical tests (one-way Analysis of Variance—ANOVA—unless stated otherwise) were performed using GraphPad Prism 6 (v6.05; GraphPad Software Inc., CA, USA), the data (were all found to be normally distributed (data not shown). For all statistical tests, p<0.05 was considered significant; data are expressed as mean±S.E.M.

Drugs and Reagents

MEM, culture serums, antibiotics, collagen, Cell Counting Kit-8 and buffers reagents were provided by Sigma-Aldrich (St. Louis, Mo.). T30, AChE peptide and Cyclic T14 were synthesized by Genosphere Biotechnologies (France). Amyloid Beta and Fluo-8 were provided by Abcam (Cambridge, UK). The small peptides were synthesized using routine peptide synthetic techniques. Stocks of peptides were diluted in distilled water.

Data Analysis

In each of the different techniques, the statistics analysis was performed with the average of the percentage values of 12 or more experiments. Comparisons between multiple treatment groups and the same control were performed by one-way analysis of variance (ANOVA) and Tukey's post-hoc tests using GraphPAD Instat (GraphPAD software, San Diego, Calif.). These tests compare the means of every treatment to the means of every other treatment; that is, apply simultaneously to the set of all pairwise comparisons and identify where the difference between two means is greater than the standard error would be expected to allow. Statistical significance was taken at a P value<0.05. Graphs were plotted using GraphPAD Prism 6 (GraphPAD software, San Diego, Calif.).

Example 1—Cyclic T14 (i.e. "NBP14")

The 'tailed' acetylcholinesterase (T-AChE) is expressed at synapses and the inventors have previously identified two peptides that could be cleaved from its C-terminus, one referred to as "T14" (14 amino acids long), within the other which is known as "T30" (30 amino acids long), and which both have strong sequence homology to the comparable region of β-amyloid.

The amino acid sequence of the linear peptide, T14, is AEFHRWSSYMVHWK [SEQ ID No:1].

The amino acid sequence of the linear peptide, T30, is

[SEQ ID No: 156]
KAEFHRWSSYMVHWKNQFDHYSKQDRCSDL.

The AChE C-terminal peptide "T14'" has been identified as being the salient part of the AChE molecule responsible for its range of non-hydrolytic actions. The synthetic 14 amino acids peptide analogue (i.e. "T14"), and subsequently the larger, more stable, and more potent amino acid sequence in which it is embedded (i.e. "T30") display actions comparable to those reported for 'non-cholinergic' AChE.

Referring first to FIGS. 1*a* and 20, there is shown the binding of a 14 amino acid long cyclic T14 peptide (i.e. "NBP-14") to the allosteric site on the α7 nicotinic-receptor to compete for binding with linear peptides T14 and T30 and also to antagonise β-amyloid. The cyclic peptide, NBP-14, is based on the amino acid sequence of T14, i.e. AEFHRWSSYMVHWK [SEQ ID No:1], but has been cyclated via the terminal Alanine (A) and Lysine (K) residues. FIG. 1*b* shows an enlarged view of the 3D structure of cyclic NBP-14 sitting in the binding pocket of the α7 nicotinic-receptor.

Figures 1, 2, 3:
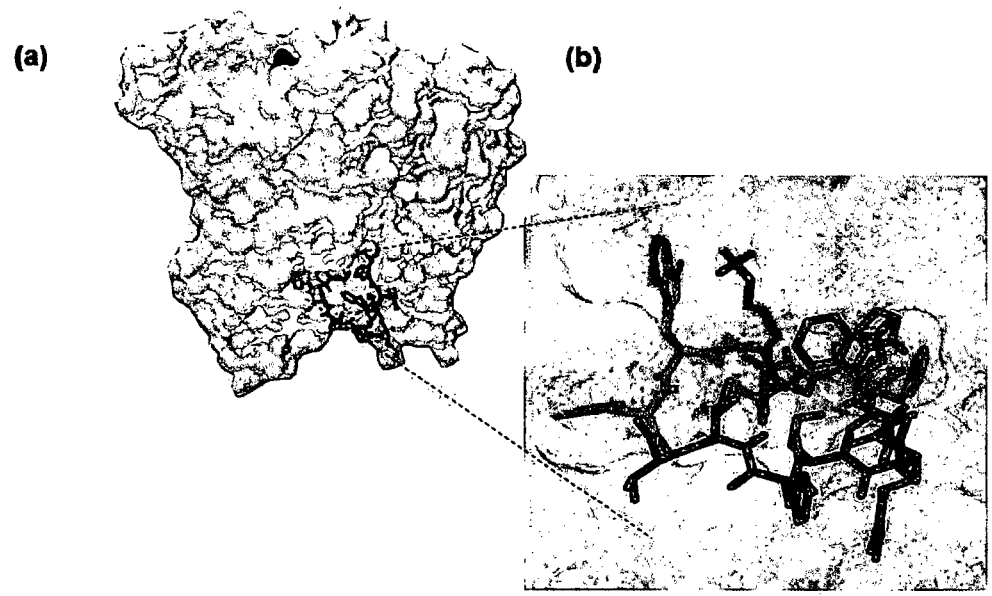
FIG. 2 shows the sequence of NBP-14 with the terminal Alanine (A) and Lysine (K) residues forming the cyclisation sites.
FIG. 3 shows the cyclic NBP-14 peptide in which the terminal Alanine and Lysine residues are linked together.

Referring now to FIG. 2, there is shown the sequence of NBP-14 with the terminal Alanine (A) and Lysine (K) residues forming the cyclisation sites, and FIG. 3 shows the cyclic NBP-14 peptide in which the terminal Alanine and Lysine residues are linked together. Cyclisation can be achieved by several different means. For example, Genosphere Biotechnologies (France) performed the cyclisation of T14 by transforming the linear peptide into an N-terminal to C-terminal lactam. Cyclisation of T14 to create cyclic NBP14 brings together both ends, i.e. HWK-AEF.

The inventors have previously shown that cyclic NBP-14 selectively inhibits the non-classical effects of AChE (i.e. the effects of AChE that are independent of its enzymatic activity) and/or its terminal peptide in vitro, and can be used to treat neurodegenerative disorders. NBP14 acts as a true antagonist of the α7 nicotinic-receptor, and has been shown to protect cells from linear T14, T30 and β-amyloid toxicity. It also blocks compensatory AChE release induced by the toxicity of linear T14 and T30. In addition, when given alone, cyclic NBP14 has no significant effects on $Ca^{2+}$ concentrations in rat brain slices, but blocks the effects of β-amyloid.

Example 2—Production of an Array of Linear Peptides Derived from Cyclic NBP14

Based on their previous surprising observations with NBP-14 discussed in Example 1, the inventors prepared an array of linear peptides (4-14 amino acids in length) based on the sequence of NBP14 in which each linear peptide sequence starts or ends at any amino acid position along the sequence of NBP14. The array of linear peptides is shown in the large table spanning FIGS. 4a-4k (identified as SEQ ID No's:2-155).

The table of FIG. 4a lists 14 linear peptides (SEQ ID No's:2-15) each of which are four amino acids in length. Each linear peptide is given a name, for example NBP-401, which signifies that it is the first peptide with four amino acids, and NBP-402, which is the second peptide with four amino acids, and so on. The table of FIG. 4b lists 14 linear peptides (SEQ ID No's:16-29) each of which are five amino acids in length. Each linear peptide in this table is given a name, for example NBP-501, which signifies that it is the first peptide with five amino acids, and NBP-502, which is the second peptide with five amino acids, and so on. FIG. 4c lists the 14, six amino acid long peptides (SEQ ID No's:30-43), FIG. 4d lists the 14, seven amino acid long peptides (SEQ ID No's:44-57), FIG. 4e lists the 14, eight amino acid long peptides (SEQ ID No's:58-71), FIG. 4f lists the 14, nine amino acid long peptides (SEQ ID No's:72-85), FIG. 4g lists the 14, ten amino acid long peptides (SEQ ID No's:86-99), FIG. 4h lists the 14, eleven amino acid long peptides (SEQ ID No's:100-113), FIG. 4i lists the 14, twelve amino acid long peptides (SEQ ID No's:114-127), FIG. 4j lists the 14, thirteen amino acid long peptides (SEQ ID No's:128-141), and FIG. 4k lists the 14, fourteen amino acid long peptides (SEQ ID No's:142-155).

Each of the linear peptides were synthesized, and then analysis for their activities as below.

Example 3—Effect of Small Linear Peptides Derived from NBP-14 on to or Aβ Toxicity and Cell Viability Each of the small linear peptides derived from NBP-14 (SEQ ID No's:2-155) were analysed with three in vitro systems against the toxic T30 linear peptide [SEQ ID No:156] and wild-type Amyloid Beta (1-42) (Aβ) (SEQ ID No:158), i.e. (i) AChE release from PC12 cells, (iii) PC12 cell viability; and (iii) calcium influx into PC12 cells.

The amino acid sequence of part of 1-amyloid (Aβ) is provided herein as SEQ ID No:158, as follows: DAEFRHDSGYEVHHQKLVFFAEDVGSNKGAIIGLMVGGVVIA [SEQ ID No:158].

The protective or toxic effect of each linear peptide against T30 and/or Aβ was then determined based on a series of four filters or criteria, as summarised in FIG. 7:—

1. AChE release vs PC12 cell viability (for which there is a significant negative correlation);
2. In silico binding to the allosteric site of the α7 nicotinic-receptor;
3. Calcium influx into PC12 cells; and
4. Peptide size.

Filter 1—AChE Release Vs PC12 Cell Viability

Initially, due to its correlation, the inventors combined assays (i) and (ii) using the equation below in order to obtain a "value coefficient (X)" that indicates the protective or toxic effect of each linear peptide against T30 and/or Aβ. The inventors determined the VALUE coefficient (X), which is calculated as:

VALUE COEFFICIENT(X)=(% AChE release)/(% Cell viability)

, wherein "% AChE release" is the percentage of acetylcholinesterase released from a PC12 cell preparation cultured in the presence of a toxic peptide selected from T30 (SEQ ID No: 156) or Aβ (SEQ ID No:158), and the peptide, derivative or analogue thereof, compared to that of the PC12 cell preparation cultured in the absence of any peptide, derivative or analogue thereof (i.e. control), and "% PC12 cell viability" is the percentage viability of the PC12 cell preparation cultured in the presence of the toxic peptide selected from T30 (SEQ ID No: 156) or Aβ (SEQ ID No:158), and the peptide, derivative or analogue thereof, compared to that of a PC12 cell preparation cultured in the absence of any peptide, derivative or analogue thereof (i.e. control).

As described below, the inventors have surprisingly shown that it is possible to separate active from inactive peptides based on their value coefficients (X) which represent their protective efficacy against T30 and Aβ toxicity.

The control (i.e. absence of any peptide) has a value of 1. As described in the methods section, the control value is obtained from cells non-treated, the toxic value from cells treated with T30 or Aβ, and the protective value from cells treated with NBP-14 in conjunction with T30 or Aβ. The value for T30 is x=169.45/74.309=2.28, and for Amyloid Beta (Aβ) x=124.19/87.42=1.42.

Hence, a peptide with a value coefficient (X) of under 1.0 and over 1.1 is toxic, whereas any peptide with a value coefficient of 1.0 to 1.1 was consider active, and therefore protective. Tables 1 and 2 show the effect of the linear peptides (at a concentration of 0.5 µM) on AChE activity and PC12 cell viability against T30 and Aβ toxicity (at a concentration of 5 µM). The "Value" column shows the protective effect of each peptide.

The inventors have shown that the two parameters, AChE activity in perfusate and PC12 cell viability, are very closely inter-related with a correlation coefficient of −0.55 (n=10), which is significant at the P<0.05 level (see FIG. 6c). This initial metric of AChE release against cell viability yielded 55 successful peptides that were protective either against T30 (n=23 peptides as shown in Table 1) or Aβ (n=32 peptides as shown in Table 2).

TABLE 1

Effects of linear peptides derived from NBP-14 on T30 toxicity

| T30 + small peptides | AChE | Viability | Value AChE/ Viability | Theoretical Affinity | Calcium | Selected peptides |
|---|---|---|---|---|---|---|
| 601 | 100.99 | 93.21 | 1.08 | −7.7 | 118.37 | 601 |
| 602 | 112.32 | 107.76 | 1.04 | −8 | 169.86 | |
| 603 | 96.06 | 94.75 | 1.01 | −7.1 | 119.86 | 603 |

TABLE 1-continued

Effects of linear peptides derived from NBP-14 on T30 toxicity

| T30 + small peptides | AChE | Viability | Value AChE/ Viability | Theoretical Affinity | Calcium | Selected peptides |
|---|---|---|---|---|---|---|
| 606 | 107.88 | 102.57 | 1.05 | −8.4 | 131.85 | |
| 613 | 103.45 | 103.45; 102.87 | 1 | −7.1 | 102.29 | 613 |
| 705 | 94.07 | 90.95 | 1.03 | −7.7 | 111.98 | 705 |
| 707 | 98.35 | 98.53 | 1 | −8.1 | 120.17 | |
| 708 | 97.79 | 97.79; 97.41 | 1 | −7.8 | 97.04 | 708 |
| 804 | 107.69 | 107.69; 107.20 | 1 | −7.5 | 106.7 | 804 |
| 1013 | 91.79 | 85.31 | 1.08 | −6.8 | 181.12 | |
| 1101 | 91.9 | 91.90; 89.24 | 1 | −7 | 86.58 | |
| 1102 | 104.31 | 104.31; 96.79 | 1 | −7.2 | 89.28 | 1102 |
| 1104 | 102.36 | 111.09 | 1 | −7.1 | 119.82 | 1104 |
| 1107 | 93.13 | 93.13; 94.28 | 1 | −7.5 | 95.43 | 1107 |
| 1205 | 95.79 | 89.43 | 1.07 | −7.8 | 132.71 | |
| 1212 | 88.29 | 88.29; 83.14 | 1 | −6.9 | 78 | |
| 1313 | 93.64 | 89 | 1.05 | −6.9 | 118.94 | |
| 1405 | 91.57 | 83.94 | 1.09 | −6.6 | 100.59 | |
| 1406 | 92.78 | 86.6 | 1.07 | −6.1 | 101.06 | |
| 1407 | 94.49 | 90.51 | 1.04 | −6.7 | 111.71 | |
| 1408 | 93.64 | 93.64; 86.94 | 1 | −6.8 | 80.25 | |
| 1409 | 94.85 | 94.85; 94.72 | 1 | −6.2 | 94.59 | |
| 1410 | 93.51 | 93.51; 106.80 | 1 | −6.7 | 120.09 | |

TABLE 2

Effects of linear peptides derived from NBP-14 on Aβ toxicity

| AB + small peptides | AChE | Viability | Value AChE/ Viability | Theoretical Affinity | Calcium | Selected peptides |
|---|---|---|---|---|---|---|
| 503 | 117.63 | 109.89 | 1.07 | −7.2 | 195.67 | |
| 508 | 106.06 | 97.62 | 1.09 | −8 | 120.72 | |
| 509 | 106.20 | 102.36 | 1.04 | −8 | 363.48 | |
| 510 | 104.25 | 100.92 | 1.03 | −6.6 | 167.56 | |
| 512 | 104.81 | 103.71 | 1.01 | −7.2 | 163.09 | |
| 607 | 97.53 | 94.93 | 1.03 | −7.7 | 168.97 | |
| 611 | 88.60 | 82.20 | 1.08 | −7.5 | 114.39 | 611 |
| 614 | 85.05 | 77.72 | 1.09 | −7.5 | 124.34 | |
| 709 | 108.99 | 101.56 | 1.07 | −7.6 | 288.61 | |
| 710 | 108.85 | 108.73 | 1 | −7.3 | 114.33 | 710 |
| 711 | 108.57 | 106.28 | 1.02 | −7 | 148.17 | |
| 801 | 108.63 | 102.35 | 1.06 | −7.7 | 168.66 | |
| 810 | 96.22 | 95.33 | 1.01 | −7.3 | 156.05 | |
| 905 | 106.42 | 97.24 | 1.09 | −7.1 | 194.22 | |
| 1009 | 101.23 | 97.49 | 1.04 | −7 | 255.80 | |
| 1011 | 84.13 | 81.66 | 1.03 | −7.1 | 161.87 | |
| 1108 | 82.74 | 77.72 | 1.06 | −7 | 392.11 | |
| 1112 | 98.77 | 93.37 | 1.06 | −7.2 | 127.62 | |
| 1201 | 94.84 | 93.09 | 1.02 | −7.7 | 114.35 | 1201 |
| 1203 | 99.63 | 95.50 | 1.04 | −6.5 | 192.38 | |
| 1206 | 96.92 | 93.63 | 1.04 | −7.2 | 127.27 | |
| 1207 | 94.30 | 87.36 | 1.08 | −6.9 | 261.22 | |
| 1210 | 98.18 | 97.55 | 1.01 | −6.8 | 127.83 | |
| 1213 | 93.73 | 90.77 | 1.03 | −6.6 | 146.97 | |
| 1214 | 89.28 | 85.51 | 1.04 | −7.1 | 217.64 | |
| 1303 | 96.73 | 91.22 | 1.06 | −6.5 | 106.33 | |
| 1307 | 94.29 | 92.47 | 1.02 | −6.9 | 218.25 | |
| 1311 | 93.51 | 86.13 | 1.09 | −6.6 | 137.63 | |
| 1314 | 104.08 | 97.90 | 1.06 | −7.2 | 130.85 | |
| 1402 | 99.85 | 91.59 | 1.09 | −7 | 127.81 | |
| 1410 | 93.51 | 93.51 | 1 | −6.7 | 160.54 | |
| 1413 | 99.85 | 95.17 | 1.05 | −6.8 | 125.28 | |

Filter 2—in Silico Binding

The inventors then examined the theoretical in silico binding affinity of the active peptides to the allosteric site of α7 nicotinic-receptor, and the values are also shown in Tables 1 and 2. The in silico analysis was performed using the Autodock Vina software published in Journal of Computational Chemistry (O. Trott, A. J. Olson AutoDock Vina: improving the speed and accuracy of docking with a new scoring function, efficient optimization and multithreading, Journal of Computational Chemistry 31 (2010) 455-461). The analysis was performed as recommended by the authors. The results analysis and the comparison were performed manually comparing the amino acids bound to the receptor and the distances between amino acids.

They found that a theoretical binding affinity inferior to −7.0 corresponded to higher affinity between the peptide and the allosteric site of α7 nicotinic-receptor. Hence, the total number of active peptides was reduced from 55 based on filter 1, down to 28 peptides following filter 2.

Filter 3—Calcium Influx

The inventors also investigated the relationship between cell viability and the third parameter (iii) discussed above, i.e. calcium influx into PC12 cells. However, they found that these parameters, which have very different time scales, are not linked, having a correlation coefficient of only 0.026 (n=10), as shown in FIG. 6b. The inventors also investigated the relationship between AChE activity and calcium influx into PC12 cells. However, they found that these parameters, again over different time scales, are also not linked, having a correlation coefficient of only 0.21 (n=10), as shown in FIG. 6a.

Accordingly, the inventors hypothesise that the release of AChE is most likely a direct 'compensation' due to eventual cell death, and not caused by non-specific, immediate entry of calcium, but instead to a slower intracellular cascade.

The values of calcium influx for the 28 peptides produced by filter 2 are also shown in Tables 1 and 2. The inventors found that a calcium influx value of 97 to 120 corresponded to active peptides. Hence, the total number of active peptides was reduced from 28 based on filter 2, down to 12 peptides following filter 3.

Filter 4—Peptide Size

Finally, the inventors believe that any peptide that is larger than 8 amino acids (theoretical molecular weight superior to 900 Da) does not present a realistic lead compound candidate for treating neurodegenerative disorders. Accordingly, these larger peptides were discounted. Hence, the total number of active peptides was reduced from 12 based on filter 3, down to 8 peptides following filter 4.

CONCLUSIONS

As such, when all four filters are taken into consideration, the number of possible neuroprotective agents against T30 is six peptides (i.e. NBP-601, 603, 613, 705, 708, and 804), and the number of agents against Aβ is only two peptides (i.e. NBP-611 and 710). Tables 1 and 2 show the green values corresponding to the protective or active peptides, whereas the red values are the toxic or inactive peptides.

Accordingly, use of the combined filters enables the isolation of neuroprotective linear peptides by structure as well as by mechanism or function. As such, the inventors are confident of their efficacy in vivo.

Example 4—Combination Therapy Using Linear Peptides

The inventors have clearly demonstrated that a small subset of the linear peptides derived from cyclic NBP-14 show surprising protective activity against T30 toxicity, and that another subset of peptides are protective against Aβ. It will be appreciated that Aβ is currently the more commonly accepted mechanism of toxicity for causing neurodegenerative disorders, such as Alzheimer's disease. Accordingly, one or more of the peptides NBP-611 and 710 are especially useful for treating neurodegenerative disorders.

However, the inventor's previous work would suggest that T30 toxicity is in fact the more likely cause for such diseases, and not Aβ toxicity. Accordingly, one or more of the peptides NBP-601, 603, 613, 705, 708, and 804 are especially useful for treating neurodegenerative disorders.

In some embodiments, the inventors believe that it would be beneficial to administer two peptides, one from the T30 protective group shown in Table 1 and one from the Aβ protective group shown in Table 2. For example, NBP-601 could be co-administered with NBP-611, or NBP-705 can be co-administered with NBP-710, and so on.

Example 5—Binding Affinity Analyses

Referring to FIGS. 5 and 20, there is shown a graphical representation of the theoretical binding affinity of the peptides making up various embodiments of the linear peptides of the invention as shown in the box with the target site of the α7 nicotinic-receptor.

Example 6—Analysis of Preferred Peptides in Dose Dependent Response in PC12 Cells Against T30 and Amyloid Dose-dependent experiments were conducted with the selected small linear variants of cyclic NBP-14 against T30, and the results are shown in FIGS. 8 and 9. The results obtained show that NBP601, NBP603 and NBP613 protect against T30 effects. These experiments corroborate the results obtained on brain slices discussed in Example 7.

Example 7—Analysis of Preferred Peptides (and NBP-14 Control) in Brain Slice Experiments Against T30

FIG. 10 illustrates the position of the basal forebrain comprising the medial septum, vertical diagonal band and horizontal diagonal band. The aim of VSDI experiments was to characterise the responses evoked in basal forebrain with 30V electrical stimulation, and to see how these responses were first modulated by addition of high concentrations of T30 (2 µM; FIG. 11).

Evoked responses were indeed found to be modulated by T30 where a majority showed inhibition while some responses showed increased activity (FIG. 12). In all cases, NBP14 addition to the perfusate was found to significantly reverse any kind of change induced by T30 (FIGS. 13, 14 & 15).

Additionally, the NBP14 variant NBP-603 (FIG. 16) was tested in the same exact experimental paradigm as for NBP14. It was found that variant NBP-603 had some significant effect in reversing the changes induced by T30 (FIGS. 17 & 19).

---

The invention claimed is:

1. A method of at least one of reversing T30 or amyloid beta induced toxicity to cell viability, decreasing calcium influx, and increasing acetylcholinesterase activity, the method comprising contacting the cell with an effective amount of one or more peptides consisting of an amino acid sequence as set out in SEQ ID No: 30, 32, 40, 42, 48, 51 or 53.

2. The method according to claim 1, comprising contacting the cell with an effective amount of the peptide consisting of the amino acid sequence as set out in SEQ ID No: 30.

3. The method according to claim 1, comprising contacting the cell with an effective amount of the peptide consisting of the amino acid sequence as set out in SEQ ID No: 32.

4. The method according to claim 1, comprising contacting the cell with an effective amount of the peptide consisting of the amino acid sequence as set out in SEQ ID No: 40.

5. The method according to claim 1, comprising contacting the cell with an effective amount of the peptide consisting of the amino acid sequence as set out in SEQ ID No: 42.

6. The method according to claim 1, comprising contacting the cell with an effective amount of the peptide consisting of the amino acid sequence as set out in SEQ ID No: 48.

7. The method according to claim 1, comprising contacting the cell with an effective amount of the peptide consisting of the amino acid sequence as set out in SEQ ID No: 51.

8. The method according to claim 1, comprising contacting the cell with an effective amount of the peptide consisting of the amino acid sequence as set out in SEQ ID No: 53.

9. The method according to claim 1, comprising contacting the cell with an effective amount of the more than one peptide.

10. The method according to claim 9, wherein the one or more peptide which is protective against T30 toxicity is used in combination with the one or more peptide which is protective against Aβ toxicity.

* * * * *